US011421226B2

(12) United States Patent
Zilberzwige-Tal et al.

(10) Patent No.: US 11,421,226 B2
(45) Date of Patent: Aug. 23, 2022

(54) PROGRAMMABLE ARTIFICIAL CELL

(71) Applicant: RAMOT AT TEL-AVIV UNIVERSITY LTD., Tel Aviv (IL)

(72) Inventors: Shai Zilberzwige-Tal, Tel Aviv (IL); Ehud Gazit, Tel Aviv (IL); Johann Elbaz, Tel Aviv (IL)

(73) Assignee: RAMOT AT TEL-AVIV UNIVERSITY LTD., Tel Aviv (IL)

( * ) Notice: Subject to any disclaimer, the term of this patent is extended or adjusted under 35 U.S.C. 154(b) by 0 days.

(21) Appl. No.: 16/654,249

(22) Filed: Oct. 16, 2019

(65) Prior Publication Data

US 2020/0123541 A1    Apr. 23, 2020

Related U.S. Application Data

(60) Provisional application No. 62/746,776, filed on Oct. 17, 2018.

(51) Int. Cl.
| | |
|---|---|
| *C12N 15/11* | (2006.01) |
| *C07H 21/02* | (2006.01) |
| *C12M 1/40* | (2006.01) |
| *C12Q 1/6865* | (2018.01) |
| *C12M 1/00* | (2006.01) |
| *B01J 19/00* | (2006.01) |

(52) U.S. Cl.
CPC ............ *C12N 15/11* (2013.01); *B01J 19/0093* (2013.01); *C07H 21/02* (2013.01); *C12M 21/18* (2013.01); *C12M 23/34* (2013.01); *C12M 23/58* (2013.01); *C12Q 1/6865* (2013.01); *C12N 2330/30* (2013.01); *C12Y 207/07007* (2013.01)

(58) Field of Classification Search
CPC ...... C12M 21/18; C12M 23/34; C12M 23/58; C12N 11/00–18; C12N 9/1247; C12Y 207/07006; C12Q 1/6865
See application file for complete search history.

(56) References Cited

U.S. PATENT DOCUMENTS 6,670,173 B1 * 12/2003 Schels .................... C12M 21/18
435/297.5

FOREIGN PATENT DOCUMENTS

| EP | 1061128 A1 * | 12/2000 | ............ B01J 19/0046 |
|---|---|---|---|
| WO | WO-2020002598 A1 * | 1/2020 | ............ B01F 13/0809 |

OTHER PUBLICATIONS

Ciechanover et al.; "Degradation of misfolded proteins in neurodegenerative diseases: therapeutic targets and strategies". Experimental & Molecular Medicine 47, e147. (2015).

Garcia et al.; "Organismal Differences in Post-translational Modifications in Histones H3 and H4* " The Journal of Biological Chemistry vol. 282, No. 10, pp. 7641-7655.(2007).
Rio "Expression and Purification of Active Recombinant T7 RNA Polymerase from *E. coli*" Cold Spring Harb Protocol (2013).
Gibson et al.; "Enzymatic assembly of DNA molecules up to several hundred kilobases" Nature Methods | vol. 6 No. 5 pp. 343-345 (2009).
Karzbrun et al.; Programmable on-chip DNA compartments as artificial cells Science , 345, pp. 829-832. (2014).
Bouhedda et al.; "Light-Up RNA Aptamers and Their Cognate Fluorogens: From Their Development to Their Applications" International Journal of Molecular Sciences 19, 44. (2018).
Katzen et al.; "The past, present and future of cell-free protein synthesis" TRENDS in Biotechnology vol. 23 No. 3. pp. 150-156. (2005).
Garamella et al.; "The All *E. coli* TX-TL Toolbox 2.0: A Platform for Cell-Free Synthetic Biology" ACS Synthetic Biology 5, pp. 344-355. (2016).
Kim et al.; "Direct Profiling the Post-Translational Modification Codes of a Single Protein Immobilized on a Surface Using Cu-free Click Chemistry" ACS Central Science 4, pp. 614-623 (2018).
Pardee et al.; "Paper-Based Synthetic Gene Networks" Cell 159, pp. 940-954. (2014).
Aufinger et al.; "Arlificial Gel-Based Organelles for Spatial Organization of Cell-Free Gene Expression Reactions"Angew Chem Int Ed Engl 57, pp. 17245-17248. (2018).
Kalia et al.; "Ubiquitinylation of a-Synuclein by Carboxyl Terminus Hsp70-lnteracting Protein (CHIP) Is Regulated by Bcl-2- Associated Athanogene 5 (BAG5)" PLoS One , 6, e14695. (2011).
Jewett et al.; "In vitro integration of ribosomal RNA synthesis, ribosome assembly, and translation" Molecular Systems Biology 9; 678. (2013).
Smanski et al.; "Synthetic biology to access and expand nature's chemical diversity" Nature Reviews 14, pp. 135-149. (2016).
Pfammatter et al.; "Absolute Quantification of Amyloid Propagons by Digital Microfluidics" Analytical Chemistry, 89, pp. 12306-12313 (2017).
Nirenberg et al.; Proc Natl Acad Sci U S A, 47, pp. 1588-1602. (1961).
Arosio et al.; "Microfluidic Diffusion Analysis of the Sizes and Interactions of Proteins under Native Solution Conditions" ACS Nano 10, pp. 333-341. (2016).
Dudley et al.; "Cell-free metabolic engineering: Biomanufacturing beyond the cell" Biotechnology Journal 10, pp. 69-82. (2015).
Moore et al.; "Rapid acquisition and model-based analysis of cell-free transcription-translation reactions from nonmodel bacteria" PNAS vol. 115. No 19 pp. E4340-E4349. (2018).
Wente et al.; "The Nuclear Pore Complex and Nuclear Transport" The Nuclear Pore Complex and Nuclear Transport. (2010).
Zilberzwige-Tal et al.; "Go with the Flow—Microfluidics Approaches for Amyloid Research" Chem. Asian J. 13, pp. 3437-3447. (2018).

(Continued)

*Primary Examiner* — Thane Underdahl
(74) *Attorney, Agent, or Firm* — Browdy and Neimark, PLLC

(57) ABSTRACT

The present invention provides cell-free systems comprising: (i) a transcription compartment; (ii) a barrier; and (iii) a translation compartment, methods for producing proteins and performing post-translational modifications thereon using such systems, and kits comprising such systems.

33 Claims, 13 Drawing Sheets
Specification includes a Sequence Listing.

(56) References Cited

OTHER PUBLICATIONS

Saggio et al.; "Biotin binders selected from a random peptide library expressed on phage" Biochem. J. 293, pp. 613-616. (1993).
Dawson et al.; "Molecular Pathways of Neurodegeneration in Parkinson's Disease" Science vol. 302 31 pp. 819-822. (2003).
Trantidou et al.,"Engineering Compartmentalized Biomimetic Micro- and Nanocontainers" American Chemical Society 11, pp. 6549-6565. (2017).
Noireaux et al.; "A vesicle bioreactor as a step toward an artificial cell assembly" PNAS , 101, pp. 17669-17674. (2004).
Kightlinger et al.; "Design of glycosylation sites by rapid synthesis and analysis of glycosyltransferases" Nature Chemical Biology vol. 14 pp. 627-635. (2018).
Heyman et al.; "Cell-free protein synthesis and assembly on a biochip" Nature Nanotechnology vol. 7 pp. 374-378. (2012).
Iwane et al.; "Expanding the amino acid repertoire of ribosomal polypeptide synthesis via the artificial division of codon boxes" Nature Chemistry vol. 8, pp. 317-325 (2016).
Shimizu et al.; "Yoshihiro Shimizu , Yutetsu Kuruma , Takashi Kanamori, and Takuya Ueda" Methods Mol Biol, 1118, pp. 275-284. (2014).

\* cited by examiner

```
        10          20          30          40          50          60          70          80
MDVFMKGLSK AKEGVVAAAE KTKQGVAEAA GKTKEGVLYV GSKTKEGVVH GVATVAEKTK EQVTNVGGAV VTGVTAVAQK
        90         100         110         120         130         140
TVEGAGSIAA ATGFVKKDQL GKNEEGAPQE GILEDMPVDP DNEAYEMPSE EGYQDYEPEA
```

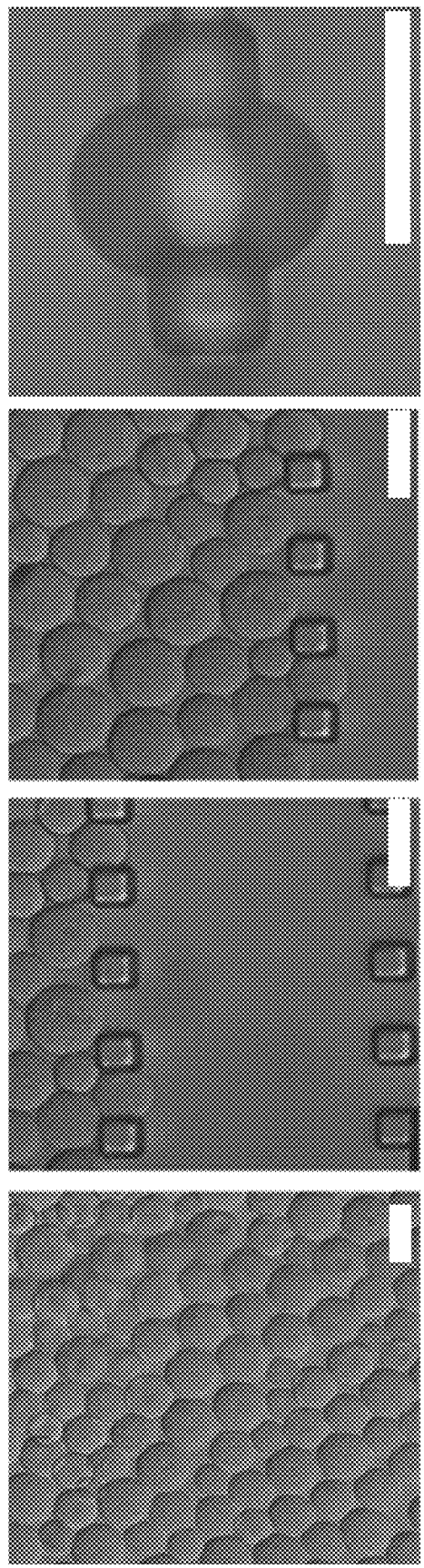

PROGRAMMABLE ARTIFICIAL CELL

CROSS REFERENCE TO RELATED APPLICATIONS

The present application claims the benefit of U.S. Provisional Application No. 62/746,776 filed Oct. 17, 2018. Any and all applications for which a foreign or domestic priority claim is identified above and/or in the Application Data Sheet as filed with the present application are hereby incorporated by reference under 37 CFR 1.57.

The Sequence Listing in ASCII text file format of 5,630 bytes in size, created on Jul. 16, 2021, with the file name "2021-07-16SequenceListing_ZILBERZWIGE1A," filed in the U.S. Patent and Trademark Office on Jul. 16, 2021, is hereby incorporated herein by reference.

FIELD OF THE INVENTION

The present invention relates in general to protein production. More specifically, to protein production in a cell-free system. Even more specifically to cell-free systems, methods and kits for producing proteins and optionally for post-translational modifications thereof.

BACKGROUND

In living cells proteins function together as the basic machinery of life. The production of functional proteins can be partitioned to specific hierarchical steps known as central dogma activities, comprising transcription, translation and post-translational modifications (PTMs). These highly coordinated biochemical processes rely on the subdivision of the reactions into different cellular compartments, allowing precise control over the final products. In particular, site-specific PTMs, such as phosphorylation, glycosylation and ubiquitination, allow to further extend the functionality of proteins by yielding a wide range of protein variants consisting of the same amino acid sequences. While this set of discrete reactions has naturally evolved over millions of years, synthetic approaches aimed to allow such control have been recently developed to generate cell-free artificial cell platforms (L. Aufinger et al., 2018; E. Karzbrun et al., 2014; V. Noireaux et al., 2004; and T. Trantidou et al., 2017).

One of the main advantages of cell-free systems (CFSs) is the reduction of the intricate cellular environment into its essential components (J. Garamella et al., 2016 and S. J. Moore et al., 2018). Since their original impact in elucidating the genetic code (M. W. Nirenberg et al., 1961), CFSs have been proven as an effective method to address fundamental questions in biology (F. Katzen et al., 2005). Moreover, CFSs have been used as a powerful synthetic biology tool allowing the production of complex molecules beyond those produced by purely synthetic chemistry, leading to the development of unprecedented therapeutic and diagnostic applications (Q. M. Dudley et al., 2015; Y. Heyman et al., 2012; Y. Iwane et al., 2016; M. C. Jewett et al., 2013; W. Kightlinger et al., 2018; and K. Pardee et al., 2014).

However, utilizing artificial cells as fully compartmentalized and controlled platforms, allowing to spatially and temporally segregate central dogma activities, remains challenging. Specifically, current artificial cell systems require elaborate procedures with multiple steps, and they also lack the ability to perform PTMs. When PTMs are synthetically introduced in an indiscriminate manner, their effect on a single protein is highly difficult to profile and characterize (K. L. Kim et al., 2018). Moreover, PTMs vary between different organisms, and while human proteins can be exogenously expressed in various in vivo models, such modifications may alter the expressed proteins characteristics compared to their original form (B. A. Garcia et al., 2007).

It thus evident that there remains an unmet need for artificial cell systems capable of performing both protein synthesis in a simple manner and further perform PTMs in a controllable manner.

SUMMARY

In one aspect, the present invention provides a cell-free system 100 comprising: (i) a transcription compartment 101 for DNA transcription, designed to bind an RNA polymerase or retain microbeads capable of binding an RNA polymerase, the compartment 101 comprises a fluid inlet port 101*a* and a fluid outlet port 101*b*; (ii) a barrier for selectively preventing or substantially decreasing passage of DNA or modified-DNA therethrough, wherein the barrier is designed to bind a molecule capable of selectively binding DNA or modified-DNA, or retain microbeads capable of binding the molecule, and the barrier is fluidly connected to or comprised within the compartment 101; and (iii) a translation compartment 102 for translation of mRNA to protein and optionally for post-translational modification of the protein, the compartment 102 comprises a fluid inlet port 102*a* that is fluidly connected to the outlet port 101*b* or the barrier, and a fluid outlet port 102*b*, wherein the compartment 102 is designed to bind the protein or retain microbeads capable of binding the protein, wherein: (a) an inner surface of the transcription compartment 101 comprises a first functional group of a specific binding pair capable of binding to a complementary second functional group of the binding pair present on the RNA polymerase, and is therefore designed to bind to the RNA polymerase; or (b) the transcription compartment 101 comprises a physical obstacle designed to prevent passage of the microbeads, if present, therethrough, and therefore retain the RNA polymerase bound to the microbeads.

In an additional aspect, the present invention provides a method of producing a protein, the method comprising: providing a cell-free system 100 according to any of the embodiments below; (ii) injecting DNA or modified-DNA into the fluid inlet port 101*a* of the compartment 101; (iii) incubating the system 100 for a sufficient time and temperature for transcription of said DNA to mRNA; (iv) injecting washing buffer into the fluid inlet port 101*a* to separate newly produced mRNA from the DNA or modified-DNA and transferring the mRNA to the translation and PTM compartment 102; (v) incubating the system 100 for a sufficient time and temperature for enabling translation of the mRNA into protein; and (vi) injecting elution buffer to elute the (bound) protein, wherein: (a) if the system 100 does not comprise an RNA polymerase, the method includes a step of injecting RNA polymerase or microbeads with an RNA polymerase bound thereon into the fluid inlet port 101*a*, after step (i) and prior to step (ii); (b) if the system 100 does not comprise a DNA-binding molecule/member, the method includes a step of injecting microbeads with a binding molecule capable of selectively binding DNA or modified-DNA into a fluid inlet port of the compartment 101 or a separate barrier compartment prior to step (iv); (c) if the system 100 does not comprise a protein-binding molecule/element, the method includes a step of injecting microbeads capable of binding the produced protein obtained in step (v), into the translation compartment 102 prior to step (v); and (d) if the system 100 does not comprise ribosomes and reagents necessary for mRNA translation, the method includes a step of injecting ribosomes and reagents necessary for mRNA translation into the translation compartment 102, prior to step (v), thereby producing the protein.

In a further aspect, the present invention provides a method for producing a post-translational modified (PTM) protein, the method comprises all the above mentioned steps for the method for producing a protein, and further comprises the following steps, after step (v) and prior to step (vi): (a) injecting wash buffer into the fluid inlet port 102a of the compartment 102 to remove cell-free translation components and mRNA; (b) injecting post-translation modification enzyme(s) and substrate (if needed) into the translation and PTM compartment 102, if the system 100 does not comprise same; (c) incubating the system 100 for a sufficient time and temperature for allowing the PTM to occur; and (d) injecting wash buffer into the fluid inlet port of the compartment 102 to remove post-translation modification enzyme(s) and substrate(s); thereby producing the post-translation modified protein.

In yet another aspect, the present invention provides a kit comprising: (i) the cell-free system 100 of the invention; and (ii) a leaflet with instructions for expressing a DNA molecule and optionally performing PTM using the cell-free system 100.

BRIEF DESCRIPTION OF DRAWINGS

FIG. 1A is an illustration of eukaryotic cell compartmentalized expression process of two genes in response to promotor activation. Following transcription in the nucleus (dashed grey line), RNA transcripts are transported to the cytoplasm, where they undergo translation and PTMs. FIG. 1B is a schematic of compartmentalization expression process in a system of the invention showing parallel transcription of two genes encoding for His-tagged proteins at two spatially separated compartments. Transcription is performed by an immobilized T7RP trapped in the compartments. Closing the valve following transcription allows RNA transcripts from either one compartment or both to flow into a downstream compartment. DNA molecules are then immobilized, while RNA molecules encounter cell-free translation components. The resulting translated His-protein is immobilized using trapped Ni beads, allowing the removal of translation components and the subsequent introduction of PTMs enzymes of choice. Following incubation, PTMs enzymes are washed and the purified proteoform is eluted. FIG. 1C is a blueprint of a system according to one embodiment of the invention showing two separate identical compartmentalization compartments on a single chip.

FIG. 2A: (i) Schematics of the two parallel transcription compartments; (ii) Schematics and bright field imaging of His-T7RP immobilized onto Ni beads trapped by pillars in the transcription compartments. Scale bar, 50 μm; and (iii) Fluorescent image of mango RNA aptamer in the detection channel. Scale bar, 100 μm. FIG. 2B: Fluorescence measurements of mango RNA light up aptamer and eGFP transcripts utilizing immobilized T7RP, using both biotinylated and non-biotinylated PCR products as templates; FIG. 2C: Alternations in two controlled mechanical promotor-like valves resulting in an oscillating switch; FIG. 2D-2E: Gradual accumulation of RNA transcripts demonstrating control over promotor strength of either two different (D) or a single (E) RNA aptamer transcript.

FIG. 3A: (i) Schematics of a system of the invention combining three hierarchical compartments. Confinement of processes in each compartment is secured by valves (red). Separate inlets allow the introduction of additional reagents. (ii) Biotinylated DNA template encoding for His-tagged protein is injected into the transcription compartment containing immobilized T7RP. Following transcription, biotinylated DNA molecules and RNA transcripts are flown to the RNA transport compartment where biotinylated DNA molecules are immobilized on trapped immobilized streptavidin (SA)-beads, allowing RNA transcripts to continue to the translation compartment. Next, newly translated His-protein is immobilized onto Ni beads trapped in the translation and PTMs compartment, allowing the removal of translation components and PTMs enzymes. (iii). Fluorescent image of His-eGFP bound to Ni beads in the translation compartment. Scale bar, 100 μm. FIG. 3B: Fluorescence spectrum and Western blot (inset) of (1) purified His-eGFP, (2) collected flow-through, and (3) elution fraction. FIG. 3C: Western blot analysis of ubiquitinated α-synuclein produced by the system of the invention: Left—anti α-synuclein; Right—anti-ubiquitin. FIG. 3D: newly identified CHIP E3 ligase ubiquitination sites denoted on the α-synuclein protein sequence (SEQ ID NO: 11) (red arrows). FIG. 3E: Hydrodynamic radius measurements of ubiquitinated α-synuclein following different incubation times, compared to pure α-synuclein and pure ubiquitin. FIG. 3F show tubes containing in vitro translated (IVT) flow-through and elution fractions of translated His-tagged eGFP corresponding to the fractions presented in FIG. 3B.

FIGS. 4A-4D show micorgraphs depicting Ni beads trapped inside the system of the invention: FIGS. 4B-4D show the physical barriers in the system in the form of pillars, preventing Ni beads to transfer. Images were obtained using a Nikon Eclipse Ti-E inverted microscope, scale bars 50 μm.

DETAILED DESCRIPTION

In nature, intracellular micro-compartments have evolved to allow the simultaneous execution of tightly regulated complex processes within a controlled environment. This architecture serves as the blueprint for the construction of a wide array of artificial cells. However, such systems are inadequate in their ability to confine and sequentially control multiple central dogma activities, i.e. transcription, translation and post-translational modifications, which results in a limited production of complex biomolecules.

The present invention is the first to provide an artificial cell-on-a-chip platform comprising hierarchical compartments allowing the processing and transport of products from transcription, through translation and to post-translational modifications, in a single system through connecting channels. This platform generates a tightly controlled system, yielding directly a purified modified protein, with the potential to produce proteoform of choice. Using this platform, we generated, in a single device, the full ubiquitinated form of the Parkinson's disease-associated α-synuclein starting from DNA. By bringing together all central dogma activities in a single controllable platform, this approach opens up new possibilities for the synthesis of complex targets, will allow deciphering diverse molecular mechanisms in health and disease and to engineer protein-based materials and pharmaceutical agents.

Figure 1A:
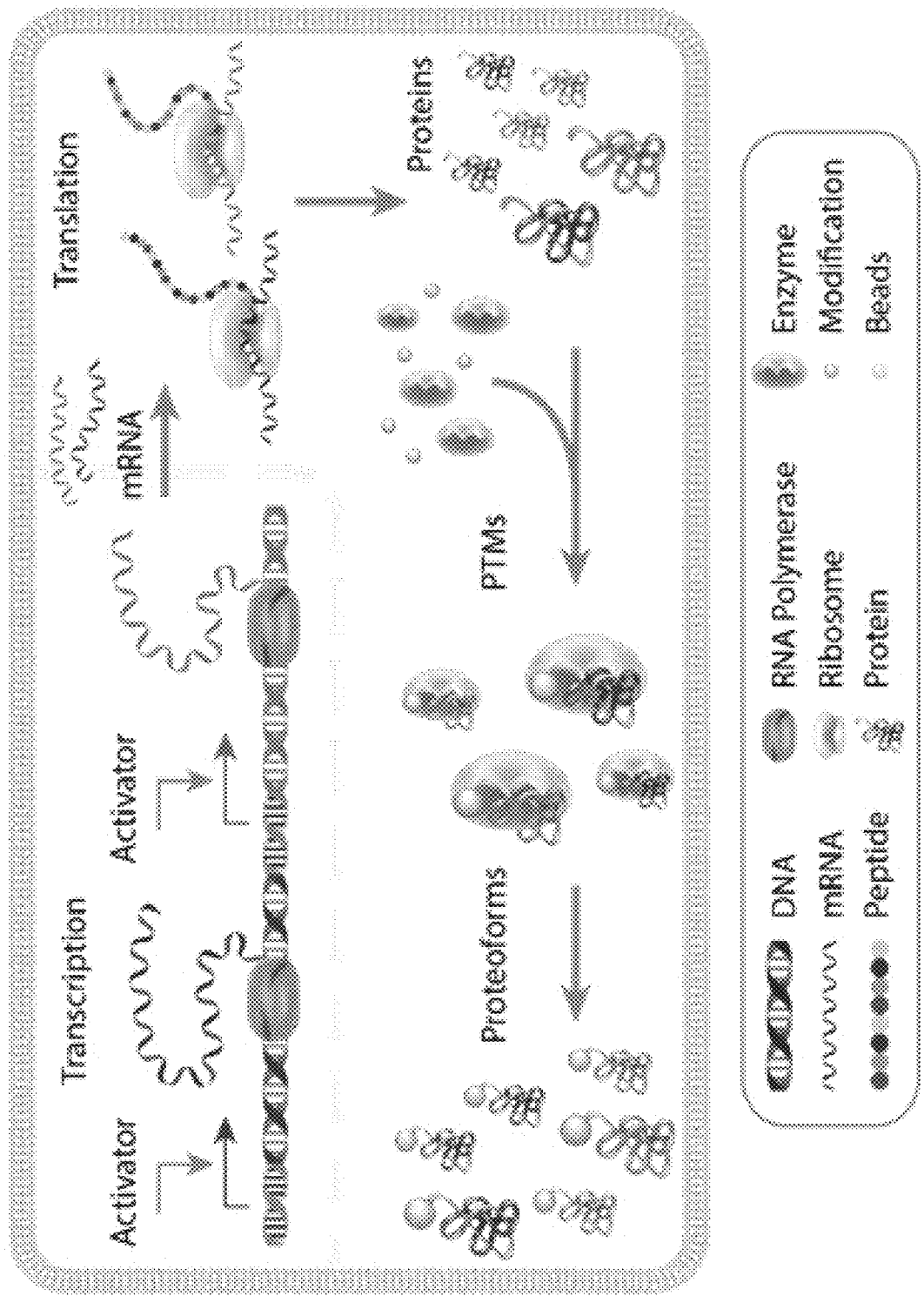
FIGS. 1A-1C show cellular processing of transcription, translation and post-translational modifications (PTMs).

The present invention provides an artificial-cell-on-chip engineered in a modular and programmable manner to control each of the central dogma activities. The system of the invention, also referred to herein interchangeably as "the CONTRALL system" (COmpartmentalized ceNTRal dogma activities Artificial ceLL), "the CONTRALL biochip", or "biochip", allows the production of proteins and modified proteins by programming transcription, translation and PTMs in a discrete and highly precise manner (FIG. 1). The system/CONTRALL enables de-coupling of transcription from translation and control over the translation time of specific RNA transcripts. In addition, de-coupling these processes allows selective and simple control over transcription activation, thus making screening of synthetic promotor libraries or designing complicated genetic circuits redundant.

Accordingly, the present invention provides a cell-free system 100 comprising: (i) a transcription compartment 101 for DNA transcription, designed to bind an RNA polymerase or retain microbeads capable of binding an RNA polymerase, the compartment 101 comprises a fluid inlet port 101a (through which DNA and optionally the RNA polymerase are inserted) and a fluid outlet port 101b (through which mRNA exits); (ii) a barrier for selectively preventing or substantially decreasing passage of DNA or modified-DNA, (but not RNA produced/transcribed in the compartment 101), therethrough, wherein the barrier is designed to bind a molecule capable of selectively binding DNA or modified-DNA, or retain microbeads capable of binding the molecule, and the barrier is fluidly connected to or comprised within the compartment 101; and (iii) a translation compartment 102 for translation of mRNA to protein and optionally for post-translational modification (PTM) of the protein, the compartment 102 comprises a fluid inlet port 102a that is fluidly connected to the outlet port 101b or the barrier, and a fluid outlet port 102b, wherein the compartment 102 is designed to bind the protein or retain microbeads capable of binding the protein, wherein: (a) an inner surface of the transcription compartment 101 comprises a first functional group of a specific binding pair capable of binding to a complementary second functional group of the binding pair present on the RNA polymerase, and is therefore designed to bind to the RNA polymerase; or (b) the transcription compartment 101 comprises a physical obstacle designed to prevent passage of the microbeads, if present, therethrough, and therefore retain the RNA polymerase bound to the microbeads.

In some embodiments of the system 100 of the invention, the first functional group and the second functional group of the binding pair are for example, but not limited to, (i) reactive groups of a click chemistry reaction; (ii) a biotin and a biotin-binding peptide or biotin-binding protein (e.g. streptavidin); (iii) metal and metal-binding peptide; and (iv) antigen and antigen-binding antibody, e.g. Flag tag, etc.

The term "binding pair" as used herein refers to a pair of different molecules, each comprising its own specific functional group, both functional groups have particular specificity for (or complimentary to) each other. In other words, these groups, under normal conditions, are capable of binding to each other in preference to binding to other molecules. The binding may be covalent or non-covalent. Non-limiting examples of such binding pairs are thiol-maleimide, azide-alkyne, aldehyde-hydroxylamine, etc.

In general, a functional group is a specific group or moiety of atoms or bonds within molecules that is responsible for the characteristic chemical reactions of those molecules. In particular, a functional group, or a functional group of a binding pair, as used herein, refers to a specific reactive group or moiety of atoms or bonds of the binding pair (herein "a first functional group") capable of binding to another functional group of the binding pair (herein "a second functional group"). As mentioned above, the first and the second functional groups are complementary to each other. Non-limiting examples of the first functional groups are thiol, azide or aldehyde and their complementary (i.e. second) functional groups are maleimide, alkyne or hydroxylamine, respectively.

It should be noted that the term "molecule capable of binding" as used herein throughout the application includes also a functional group of such a molecule.

In one embodiment, the first functional group of the specific binding pair is capable of forming a covalent bond with the complementary second functional group of the binding pair. In a particular embodiment, the covalent bond is via a click chemistry reaction.

In specific embodiments of the system 100 according to the invention, (i) the first functional group of the specific binding pair is alkyne or phosphine, and the second functional group of the binding pair is azide, or vice versa; (ii) the first functional group of the specific binding pair is cycloalkene, cycloalkyne, cyclopropane, isonitrile (isocyanide) or vinyl boronic acid, and the second functional group of the binding pair is tetrazine, or vice versa; (iii) the first functional group of the specific binding pair is alkyne or maleimide, and the second functional group of the binding pair is thiol, or vice versa; (iv) the first functional group of the specific binding pair is conjugated diene, and the second functional group of the binding pair is substituted alkene, or vice versa; (v) the first functional group of the specific binding pair is alkene, alkyne or copper acetylide, and the second functional group of the binding pair is nitrone, or vice versa; (vi) the first functional group of the specific binding pair is aldehyde or ketone, and the second functional group of the binding pair is alkoxyamine, hydroxylamine, hydrazine or hydrazide, or vice versa; (vii) the first functional group of the specific binding pair is aldehyde, ketone, isothiocyanate, carboxylic acid or derivative thereof such as ester, anhydride, acyl halide, tosyl and N-hydroxysuccinimide (NHS), and the second functional group of the binding pair is amine, or vice versa; or (viii) the first functional group of the specific binding pair is a peptide, and the second functional group of the binding pair is an antibody with high affinity for such peptide, or vice versa. In a more particular embodiment, the specific binding pair is alkyne-azide.

In certain embodiments of the system 100 according to the invention, the first functional group of the specific binding pair is capable of forming a non-covalent bond with the complementary second functional group of the binding pair. In specific embodiments, the first functional group of the specific binding pair is biotin, and the second functional group of the binding pair is its binding-partner selected from a biotin-binding peptide or biotin-binding protein, or vice versa.

In specific alternative embodiments of the system 100 of the invention, the transcription compartment 101 and the translation compartment 102 constitute the same compartment. In such a configuration, the separation of the location of the two types of microbeads is carried out by injecting into such a compartment a first type of microbeads, e.g., sodium alginate (SA)-beads, and allowing them to flow to the end of the channel/compartment where they will stop due to the presence of a physical obstacle preventing their passage, such as pillars. Then, a second type of microbeads, e.g. Ni-beads, are injected. These microbeads will migrate until they meet the first microbeads type and shall stop due to the presence of the same barrier (without the need for an extra set of pillars). In this case there will be some spatial overlap between the two types of microbeads.

In certain embodiments of the cell-free system 100 of the invention, the barrier comprises a molecule or a functional group capable of selectively binding DNA or modified-DNA, or is designed to retain microbeads comprising or capable of binding the molecule or the functional group.

In certain embodiments of the cell-free system 100 of any of the embodiments above, the compartment 101 comprises a physical obstacle designed to prevent passage of microbeads capable of binding the RNA polymerase therethrough, and the physical obstacle comprises multiple pillars, each one of which is separated from an adjacent pillar or inner surface of the compartment 101 by a space that is smaller than the microbeads' diameter. In specific embodiments, each one of the multiple pillars is a protrusion of a compartment surface, e.g. having a three-dimensional shape of a box, a pole, or a dome.

The term "inner surface" as used herein throughout the application relates to the internal surface of a compartment and/or passages within the system/biochip 100 of the invention, which are in direct contact with fluids passing therethrough. When stating that the inner surface "comprises" or "coated", it should be understood that the entire inner surface of the area or only part thereof are being coated or comprise the mentioned molecule or moiety.

In specific embodiments of the cell-free system 100 of any of the embodiments above, the compartment 101 comprises microbeads bound to or designed to bind the RNA polymerase. In alternative specific embodiments of the cell-free system 100 of any of the embodiments above, the compartment 101 lacks microbeads bound to or designed to bind the RNA polymerase, wherein such microbeads are designed to be injected into the compartment 101 prior to use thereof. In further specific embodiments, the RNA polymerase is a T7 RNA polymerase.

It should be noted that the microbeads utilized in the system 100 according to the invention for binding RNA polymerase may comprise any molecule or moiety suitable for binding the RNA polymerase. For instance, the microbeads may comprise a first functional group of a specific binding pair capable of binding to a complementary second functional group of the binding pair present on the RNA polymerase. In specific embodiments of the cell-free system 100 of any of the embodiments above, the microbeads comprise a transition metal ion having high affinity to poly-histidine sequence (His-tag); and the RNA polymerase comprises a His-tag bound to the transition metal ion, thereby immobilizing the RNA polymerase to the microbeads (or vice versa). In specific embodiments thereof, the transition metal ion is selected from the group consisting of $Ni^{2+}$, $Co^{2+}$, $Cu^{2+}$, and $Zn^{2+}$. In a specific embodiment, the transition metal ion is $Ni^{2+}$. In alternative specific embodiments of the cell-free system 100 of any of the embodiments above, the RNA polymerase comprises various tags, such as Myc-tag or Flag-tag; and the microbeads comprises antibody(s) with high affinity thereto, thereby immobilizing the RNA polymerase to the microbeads.

The term "high affinity" as used herein refers to a chemical or bio-physical association, such as chelator-metal coupling (e.g. Ni and a peptide sequence comprising several His-residues such as $His_6$), or an conjugation between two members of a binding pair, e.g. an antibody and its target epitope or biotin and streptavidin, etc., wherein the association between two binding pairs has a $K_d$ of $10^{-4}$ M to $10^{-30}$ M, e.g. $10^{-6}$ M, $10^{-7}$ M, $10^{-8}$ M, $10^{-9}$ M, $10^{-10}$ M, $10^{-11}$ M, $10^{-12}$ M or $12^{-13}$ M.

In certain embodiments, the present invention provides a cell-free system 100 of any of the embodiments above, comprising: (i) a transcription compartment 101 for DNA transcription, retaining or designed to retain microbeads capable of binding an RNA polymerase, the compartment 101 comprises a fluid inlet port 101a through which DNA and optionally the RNA polymerase are inserted, and a fluid outlet port 101b through which mRNA exits, wherein the compartment 101 comprises a physical obstacle designed to prevent passage of microbeads capable of binding the RNA polymerase, wherein the physical obstacle comprises multiple pillars, each one of which is separated from an adjacent pillar or inner surface of the compartment 101 by a space that is smaller than the microbeads' diameter; (ii) a barrier for selectively preventing or substantially decreasing passage of DNA or modified-DNA, (but not RNA produced/transcribed in the compartment 101), therethrough, wherein the barrier is designed to bind a molecule capable of selectively binding DNA or modified-DNA, or retain microbeads capable of binding the molecule, and the barrier is fluidly connected to or comprised within the compartment 101; and (iii) a translation compartment 102 for translation of mRNA to protein and optionally for post-translational modification (PTM) of the protein, the compartment 102 comprises a fluid inlet port 102a that is fluidly connected to the outlet port 101b or the barrier, and a fluid outlet port 102b, wherein the compartment 102 is designed to bind the protein or retain microbeads capable of binding the protein.

In specific embodiments, the barrier comprises a molecule or a functional group capable of selectively binding DNA or modified-DNA, or is designed to retain microbeads comprising or capable of binding the molecule or the functional group. In further specific embodiments, the barrier comprises or retains microbeads comprising or capable of binding a molecule or a functional group capable of selectively binding DNA or modified-DNA.

In certain embodiments of the cell-free system 100 of any of the embodiments above, the inner surface of the compartment 101 comprises a first functional group of a specific binding pair capable of binding to a complementary second functional group of the binding pair present on the RNA polymerase. In specific embodiments, the compartment 101 comprises the RNA polymerase linked to the first functional group via the second functional group. In specific alternative embodiments, the compartment 101 does not comprise the RNA polymerase, which is designed to be added prior to use.

In certain embodiments, the present invention provides, a cell-free system 100 of any of the embodiments above, comprising: (i) a transcription compartment 101 for DNA transcription, designed to bind an RNA polymerase, the compartment 101 comprises a fluid inlet port 101a through which DNA and optionally the RNA polymerase are inserted, and a fluid outlet port 101b through which mRNA exits, wherein the compartment 101 comprises a first functional group of a specific binding pair capable of binding to a complementary second functional group of the binding pair present on the RNA polymerase; (ii) a barrier for selectively preventing or substantially decreasing passage of DNA or modified-DNA, (but not RNA produced/transcribed in the compartment 101), therethrough, wherein the barrier is designed to bind a molecule capable of selectively binding DNA or modified-DNA, or retain microbeads capable of binding the molecule, and the barrier is fluidly connected to or comprised within the compartment 101; and (iii) a translation compartment 102 for translation of mRNA to protein and optionally for post-translational modification (PTM) of the protein, the compartment 102 comprises a fluid inlet port 102a that is fluidly connected to the outlet port 101b or the barrier, and a fluid outlet port 102b, wherein the compartment 102 is designed to bind the protein or retain microbeads capable of binding the protein.

In specific embodiments, the barrier comprises a molecule or a functional group capable of selectively binding DNA or modified-DNA, or is designed to retain microbeads comprising or capable of binding the molecule or the functional group. In further specific embodiments, the barrier comprises or retains microbeads comprising or capable of binding a molecule or a functional group capable of selectively binding DNA or modified-DNA.

In certain embodiments of the cell-free system 100 of any of the embodiments above, the barrier comprises a physical obstacle designed to prevent passage of microbeads capable of selectively binding DNA or modified-DNA, and is localized in a physical compartment 103 spatially separated from but fluidly connected to the compartment 101 and to the compartment 102. In specific embodiments, the compartment 103 further comprises the microbeads. In further specific embodiments, the microbeads are bound to a molecule capable of selectively binding DNA or modified-DNA.

In certain embodiments, the present invention provides a cell-free system 100 comprising: (i) a transcription compartment 101 for DNA transcription, designed to bind an RNA polymerase or retain microbeads capable of binding an RNA polymerase, the compartment 101 comprises a fluid inlet port 101a (through which DNA and optionally the RNA polymerase are inserted) and a fluid outlet port 101b (through which mRNA exits); (ii) a translation compartment 102 for translation of mRNA to protein and optionally for post-translational modification (PTM) of the protein, the compartment 102 comprises a fluid inlet port 102a that is fluidly connected to the outlet port 101b or the barrier, and a fluid outlet port 102b, wherein the compartment 102 is designed to bind the protein or retain microbeads capable of binding the protein; and (iii) a barrier compartment 103 spatially separated from but fluidly connected to the compartment 101 and the compartment 102 for selectively preventing or substantially decreasing passage of DNA or modified-DNA, (but not RNA produced/transcribed in the compartment 101), therethrough, wherein the barrier compartment 103 is designed to bind a molecule capable of selectively binding DNA or modified-DNA, or retain microbeads capable of binding the molecule, wherein: (a) an inner surface of the transcription compartment 101 comprises a first functional group of a specific binding pair capable of binding to a complementary second functional group of the binding pair present on the RNA polymerase, and is therefore designed to bind to the RNA polymerase; or (b) the transcription compartment 101 comprises a physical obstacle designed to prevent passage of the microbeads, if present, therethrough, and therefore retain the RNA polymerase bound to the microbeads.

In specific embodiments, the barrier compartment 103 comprises a molecule or a functional group capable of selectively binding DNA or modified-DNA, or is designed to retain microbeads comprising or capable of binding the molecule or the functional group, wherein the compartment 103 optionally comprises such microbeads.

In specific embodiments of the cell-free system 100 of any of the embodiments above, the modified-DNA is biotinylated DNA, and the molecule capable of selectively binding modified-DNA is selected from the group consisting of: a biotin-binding peptide and a biotin-binding protein; and the molecule capable of selectively binding DNA is a DNA-binding protein, such as transcription factors (repressors and activators), proteins with zinc-finger domains/leucine-zipper domain, anti-dsDNA antibodies, e.g., specific for systemic lupus erythematosus (SLE), etc. In further specific embodiments, the biotin-binding protein is streptavidin or avidin.

For example, the biotin-binding protein may be selected from avidin, streptavidin and an anti-biotin antibody; and the biotin-binding peptide is selected from AEGEFCSWAPPKASCGDPAK (SEQ ID NO: 7), CSWRPPFRAVC (SEQ ID NO: 8), CSWAPPFKASC (SEQ ID NO: 9), and CNWTPPFKTRC (SEQ ID NO: 10) (Saggio and Laufer, 1993; incorporated herein by reference as if fully enclosed). The Cysteine residues may form a disulfide bond and linkers could be attached to the N- or C-terminus, or to both termini.

In specific embodiments of the cell-free system 100 of any of the embodiments above, the physical obstacle comprises multiple pillars, each one of which is separated from an adjacent pillar or an inner surface of the compartment 103 by a space that is smaller than the microbeads' diameter.

In certain embodiments of the cell-free system 100 of any of the embodiments above, the inner surface of the barrier comprises a first functional group of a specific binding pair capable of binding to a complementary second functional group of the binding pair present on the DNA or modified-DNA, and is therefore designed to bind to the DNA or modified-DNA.

In certain embodiments of the cell-free system 100 of any of the embodiments above, an inner surface of the barrier or the compartment 103 comprises a first functional group of a specific binding pair capable of binding to a complementary second functional group of the binding pair present on the DNA or modified-DNA to thereby prevent its passage therethrough.

The term "modified-DNA" as used herein refers to any DNA that has been modified in any known technique. For instance, the DNA may be modified by the addition of a functional group, which may be a member of a binding pair. One specific example is biotinylated DNA. Other modification examples are DNA that has been Flag-tagged, or tagged with an antibody-specific molecule, covalent bonding, i.e. modifying DNA with thiol (S—H) or amine (NH$_2$) groups at their 3'- or 5'-end which enable them to bind to metal (such as gold) or to other specific functional group, etc. Another modification method is to increase the negative charge of the DNA (e.g. via charged phosphate group) and then use electrostatic adsorption technique.

In certain embodiments of the cell-free system 100 of any of the embodiments above, the translation compartment 102 comprises microbeads capable of binding the protein and a physical obstacle designed to prevent passage of the microbeads therethrough. In specific embodiments, the physical obstacle comprises multiple pillars, each one of which is separated from an adjacent pillar or an inner surface of the compartment 102 by a space that is smaller than the microbeads' diameter. In further or alternative embodiments, the protein comprises a His-tag, and the microbeads comprise a transition metal ion having high affinity to His-tag and the His-tag binds to the microbeads via the transition metal ion, thereby immobilizing the protein to the microbeads. In more specific embodiments, the transition metal ion is selected from the group consisting of $Ni^{2+}$, $Co^{2+}$, $Cu^{2+}$, and $Zn^{2+}$. In a further specific embodiment, the transition metal ion is $Ni^{2+}$.

In certain embodiments of the cell-free system 100 of any of the embodiments above, the compartment 102 further comprises ribosomes and optionally other reagents necessary for translation, e.g. a cell-free protein synthesis reagent such as PUREfrex®, a series of newly developed reconstituted cell-free protein synthesis reagent that consists of proteins, ribosome, amino acids and NTPs only. Those proteins are necessary for transcription, translation and energy regeneration. The proteins and ribosome are highly purified individually and assembled together to constitute the protein synthesis system.

In certain embodiments of the cell-free system 100 of any of the embodiments above, the inner surface of the translation compartment 102 comprises a first functional group of a specific binding pair capable of binding to a complementary second functional group of the binding pair present on the protein, and is therefore designed to bind to the protein.

In certain embodiments of the cell-free system 100 of any of the embodiments above, the translation compartment 102 is designed to bind the protein, and may have bound to a surface thereof a binding molecule/element designed to bind the protein or a tag within the protein. For example, the binding molecule/element may be an antibody specific for the protein or the tag.

In certain embodiments of the cell-free system 100 of any of the embodiments above, the compartment 102 lacks microbeads capable of binding the protein and lacks ribosomes and other reagents necessary for translation, but comprises a physical obstacle designed to prevent passage of the microbeads therethrough.

In certain embodiments, the cell-free system 100 of any of the embodiments above, further comprises at least one valve 104 that controls flow or flow rate. In specific embodiments, the cell-free system 100 comprises a single valve 104 positioned between the transcription compartment 101 and the translation compartment 102. In further specific embodiments, the single valve 104 is positioned after (at the outlet of) the translation compartment 102. In alternative embodiments, the system 100 comprises 2, 3, 4, 5 or more valves 104.

In certain embodiments, the cell-free system 100 of any of the embodiments above comprises one or more additional DNA transcription compartments 101 each comprising a fluid inlet port 101*a* and a fluid outlet port 101*b*, and fluidly connected to the translation compartment 102.

In certain embodiments, the cell-free system 100 of any of the embodiments above comprises one or more additional translation compartment 102, each fluidly connected to a different DNA transcription compartment 10.

In certain embodiments, the system 100 according to any of the embodiments above comprises a plurality of transcription compartments 101 that are fluidly connected to the same transcription translation compartment 102. In specific embodiments, the plurality of transcription compartments 101 are fluidly connected to the same transcription translation compartment 102 via the same DNA-barrier. In alternative specific embodiments, each one of the plurality of transcription compartments 101 is fluidly connected to the same transcription translation compartment 102 via a separate DNA-barrier. In specific embodiments, the system 100 comprises 2, 3, 4, 5, 6, 7, 8, 9, 10 or more transcription compartments 101.

In specific embodiments, the system 100 according to any of the embodiments above comprises two or more transcription compartments 101, the first designed to receive DNA of a desired target protein for synthesis and post-translational modification (PTM) thereof, and the other(s) designed to receive DNA encoding PTM enzyme(s) for producing such PTM enzyme(s), either within the translation compartment 102 or that will be flown therein, so that these PTM enzyme(s) will perform PTM on the target protein.

It alternative or additional specific embodiments, the system 100 according to any of the embodiments above comprises two or more transcription compartments 101, the first designed to receive DNA of a desired target protein for synthesis and optionally for post-translational modification (PTM) thereof. The remaining transcription compartment(s) 101 is/are designed to receive DNA encoding any required protein, such as PTMs or protein(s) required for hierarchical assembly of a protein complex.

In certain embodiments, the cell-free system 100 of any of the embodiments above comprises one or more additional translation compartment 102, each fluidly connected to a different DNA transcription compartments 101, each designed to produce a different protein, such as a desired target protein and post-translational modification (PTM) enzyme(s). These proteins can be flown into a new compartment or into the translation compartment 102 of the target protein for performing PTM on the target protein.

It should be noted that the cell-free system 100 according to any of the embodiments above can be fabricated in any known technique such as blow-molding, press-molding, engraving, 3-dimensional printing, soft lithography etc. It should also be noted that the cell-free system 100 according to any of the embodiments above can be fabricated from any suitable material such as glass, plastic, nylon, polydimethylsiloxane (PDMS). In specific embodiments, the entire system 100 is made from the same material. Alternatively, different compartments and passages of the system 100 are made from different materials, e.g. in order to improve binding capabilities and/or reduce impurities, etc. In specific embodiments, the inner surfaces of the system 100 are coated, e.g. with binding molecules or inert material, according to need.

In an additional aspect, the present invention provides a method of producing a protein, the method comprising: providing a cell-free system 100 according to any of the embodiments above; (ii) injecting DNA or modified-DNA into the fluid inlet port 101*a* of the compartment 101; (iii) incubating the system 100 for a sufficient time and temperature allowing the RNA polymerase to transcript mRNA; (iv) injecting washing buffer into the fluid inlet port 101*a* to separate newly produced mRNA from the DNA or modified-DNA and transferring the mRNA to the translation and PTM compartment 102; (v) incubating the system 100 for a sufficient time and temperature for allowing translation of the mRNA to protein; and (vi) injecting elution buffer to elute the (bound) protein, wherein: (a) if the system 100 does not comprise an RNA polymerase, the method includes a step of injecting RNA polymerase or microbeads with an RNA polymerase bound thereon into the fluid inlet port 101a, after step (i) and prior to step (ii); (b) if the system 100 does not comprise a DNA-binding molecule/member, the method includes a step of injecting microbeads with a binding molecule capable of selectively binding DNA or modified-DNA into a fluid inlet port of the compartment 101 or a separate barrier compartment prior to step (iv); (c) if the system 100 does not comprise a protein-binding molecule/element, the method includes a step of injecting microbeads capable of binding the produced protein obtained in step (v), into the translation compartment 102 prior to step (v); and (d) if the system 100 does not comprise ribosomes and reagents necessary for mRNA translation, the method includes a step of injecting ribosomes and reagents necessary for mRNA translation into the translation compartment 102, prior to step (v), and optionally after step (iv), thereby producing the protein.

In certain embodiments of the system 100 and method according to any of the embodiments above, the protein(s) produced in the translation compartment 102 are bound to either microbeads or to a binding molecule/element at the inner surface of the compartment 102. Accordingly, the step of elution of the final protein requires the injection of an elution buffer that releases the bound protein from the microbeads or the binding molecule/element.

In certain embodiments, the above method of producing a protein comprises the following steps: (i) providing a cell-free system 100 according to any of the embodiments above; (ii) injecting DNA or modified-DNA into the fluid inlet port 101a of said compartment 101; (iii) incubating the system 100 for a sufficient time and temperature for transcription of said DNA to mRNA; (iv) injecting washing buffer into said fluid inlet port 101a to separate newly produced mRNA from said DNA or modified-DNA and transferring said mRNA to the translation and post-translational modification (PTM) compartment 102; (v) incubating the system 100 for a sufficient time and temperature for enabling translation of said mRNA to protein; and (vi) injecting elution buffer to elute the (bound) protein, to thereby producing the protein, wherein, provided that when the system 100 does not comprise: (1) an RNA polymerase, the method further includes a step of injecting RNA polymerase or microbeads with an RNA polymerase bound thereon into said fluid inlet port 101a, after step (i) and prior to step (ii); (2) a DNA-binding molecule, the method further includes a step of injecting microbeads with a binding molecule capable of selectively binding DNA or modified-DNA into a fluid inlet port of said compartment 101 or a separate barrier compartment prior to step (iv); (3) a protein-binding molecule, the method further includes a step of injecting microbeads capable of binding the protein obtained in step (iii), into said translation compartment 102 prior to step (iv); and (4) ribosomes and reagents necessary for mRNA translation, the method further includes a step of injecting ribosomes and reagents necessary for mRNA translation into said translation compartment 102, prior to step (iv).

The term "sufficient temperature" as used herein refers to the optimal temperature in which different proteins, enzymes and various biological process are carried out for optimal results in terms of, e.g., speed and accuracy. For instance, T7 RNA polymerase usually requires 37° C. for optimal activity. The term "sufficient time" as used herein refers to the time duration in which desired results are obtained in term of amount of, e.g., desired outcome and accuracy thereof. The time may vary according to the process conditions, such as temperature, pressure etc. For instance, the optimal time for T7 RNA polymerase activity at 37° C. under normal pressure, is about 1 hour.

Accordingly, in specific embodiments of the method according to any of the embodiments above, the step of incubating the system 100 for transcription the DNA to mRNA, is for about 1 hour at about 37° C. In further specific embodiments the step of incubating the system 100 for translating the mRNA into protein(s) and also for enabling PTM of the protein, is for about 4 hour at about 37° C.

It should be noted that when the system 100 is provided with all required microbeads within it and/or with designated coatings on different inner surfaces therein with certain molecules or functional group(s), no additional injection steps are required. However, if the system is provided "blank", i.e. without any microbeads within and without any internal surface coatings, additional injection steps are required in order to add into the system 100 all components that are required for binding, e.g. the DNA or modified-DNA, the RNA polymerase, the protein(s), etc. Alternatively, the system 100 may be provided with some of these elements, in which case the method may include additional injection steps for adding any missing components into the system 100. For instance, if the system 100 does not comprise RNA polymerase, further steps of injecting RNA polymerase, either free or bound to microbeads, is required. The decision whether to inject a free element, such as the RNA polymerase, or an element bound to microbeads, is dependent on whether the system 100 comprises a first functional group of a specific binding pair capable of binding to a complementary second functional group of the binding pair present on the element being injected, or not: if there is a coating, there is no need to inject the element bound to microbeads, and if the system 100 comprise a physical obstacle, it is possible to inject the element bound to microbeads.

In certain embodiments, the method according to the invention for producing a protein, comprises the following steps: (i) providing a cell-free system 100 according to any of the embodiments above, which does not comprise protein-binding molecules/elements;

(ii) injecting microbeads capable of binding the protein, and ribosomes and reagents necessary for mRNA translation into the translation compartment 102; (iii) injecting DNA or modified-DNA into the fluid inlet port of the compartment 101; (iv) incubating the system 100 for a sufficient time and temperature for allowing the RNA polymerase to transcript mRNA; (v) injecting wash buffer into the fluid inlet port of the compartment 101 to separate newly produced mRNA from the DNA or modified-DNA and transferring the mRNA to the translation and PTM compartment 102; (vi) incubating the system 100 for a sufficient time and temperature for allowing translation of the mRNA to protein; and (vii) injecting elution buffer to elute the (bound) protein, thereby producing the protein.

In certain embodiments, the method according to the invention comprises the following steps: (i) providing a cell-free system 100 according to any of the embodiments above, which does not include RNA polymerase, DNA-binding molecule/member and protein-binding molecule/element; (ii) injecting RNA polymerase or microbeads binding an RNA polymerase into the fluid inlet port 101a of the compartment 101; (iii) injecting microbeads binding a molecule capable of selectively binding DNA or modified-DNA into a fluid inlet port of the compartment 101 or a separate barrier compartment; (iv) injecting microbeads capable of binding the protein, and ribosomes and reagents necessary for mRNA translation into the compartment 102; (v) injecting DNA or modified-DNA into the fluid inlet port of the compartment 101; (vi) incubating the system 100 for a sufficient time and temperature for allowing the RNA polymerase to transcript mRNA; (vii) injecting wash buffer into the fluid inlet port of the compartment 101 to separate newly produced mRNA from the DNA or modified-DNA and transferring the mRNA to the translation and PTM compartment 102; (viii) incubating the system 100 for a sufficient time and temperature for allowing translation of the mRNA to protein; and (ix) injecting elution buffer to elute the (bound) protein, thereby producing the protein.

In certain embodiments, the method according to any of the embodiments above for producing a protein, comprises the following additional steps after the step of translation of the mRNA into protein and prior to the step of eluting the protein from the system 100, for producing a post-translational modified (PTM) protein: (a) injecting wash buffer into the fluid inlet port 102a of the compartment 102 to remove cell-free translation components and mRNA; (b) injecting post-translation modification enzyme(s) and substrate (if needed) into the translation and PTM compartment 102, if the system 100 does not comprise same; (c) incubating the system 100 for a sufficient time and temperature for allowing the PTM to occur; and (d) injecting wash buffer into the fluid inlet port of the compartment 102 to remove post-translation modification enzyme(s) and substrate(s); thereby producing the post-translation modified protein.

In specific embodiments of the method according to any of the embodiments above, when the system 100 of the invention comprises two or more transcription compartments 101, the first designed to receive DNA of a desired target protein for synthesis and post-translational modification (PTM) thereof, and the other(s) designed to receive DNA of PTM enzyme(s) for producing such PTM enzyme(s), The method according to any of the embodiments above further includes a step of injecting DNA of such PTM enzyme(s) into one or more of the transcription compartment(s) 101, such that mRNA of these PTM enzymes can flow into the same or different translation compartment 102 as the mRNA of the target protein, for producing such PTM enzyme(s) so that they will perform PTM on the desired protein. In specific embodiments, when the cell-free system 100 comprises one or more additional translation compartment 102, each fluidly connected to a different DNA transcription compartments 101, each designed to produce a different protein, the method of the invention further includes a step of injecting DNA of both a desired target protein and post-translational modification (PTM) enzyme(s) for production thereof in different translation compartments 102. In such particular embodiment, the method further includes a step of flowing all these proteins into a new compartment or into the translation compartment 102 where the target protein was produced for performing the PTM on the target protein.

In certain embodiments, the present invention further provides a kit comprising: (i) the cell-free system 100 of claim 1; and (ii) a leaflet with instructions for expressing a DNA molecule and optionally performing PTM using the cell-free system 100.

In certain embodiments, the kit of the invention further comprises at least one of the following components: (i) a vessel comprising RNA polymerase or RNA polymerase immobilized on microbeads; (ii) a vessel comprising DNA-binding molecule/member or modified-DNA-binding molecule/member immobilized on microbeads; (iii) a vessel comprising cell-free translation components; (iv) a vessel comprising microbeads designed to immobilize protein; and (v) vessels comprising solutions comprising factors necessary for producing RNA and protein, and optionally PTM of the protein.

In certain embodiments, the kit according to any of the embodiments above further comprises at least one of the following components: (i) a vessel comprising washing solution; and (ii) a vessel comprising elution solution.

In specific embodiments, the kit according to any of the embodiments above comprises the following components: (a) the cell-free system 100 of claim 1; (b) a vessel comprising RNA polymerase immobilized on microbeads; (c) a vessel comprising DNA-binding molecule/member or modified-DNA-binding molecule/member immobilized on microbeads; (d) a vessel comprising cell-free translation components; (e) a vessel comprising microbeads designed to immobilize protein; (f) vessels comprising solutions comprising factors necessary for producing RNA and protein, and optionally PTM of the protein; (g) a leaflet with instructions for expressing a DNA molecule and optionally performing PTM using the cell-free system 100; (h) optionally, a vessel comprising washing solution; and (i) optionally a vessel comprising elution solution.

By integrating simple biosynthesis techniques, it is possible to further extend the system 100 and method of the invention to purify desired proteins on-chip, allowing dynamic modulation of PTMs of choice. As a non-limiting example, the present application demonstrates the ubiquitination of α-synuclein, a protein with notable aggregation propensity that is associated with Parkinson's disease, characterized the reaction products and identified the ubiquitination sites. It has thus been found in accordance with the present invention that by modulating the substrates used in the reaction, the CONTRALL platforms/system 100 according to the invention allows for precise PTMs to be incorporated within the protein's sequence in a selective manner. This dynamic approach, as sown for α-synuclein, can be applied to a wide range of existing cell-free protein-based systems.

Figure 1B:
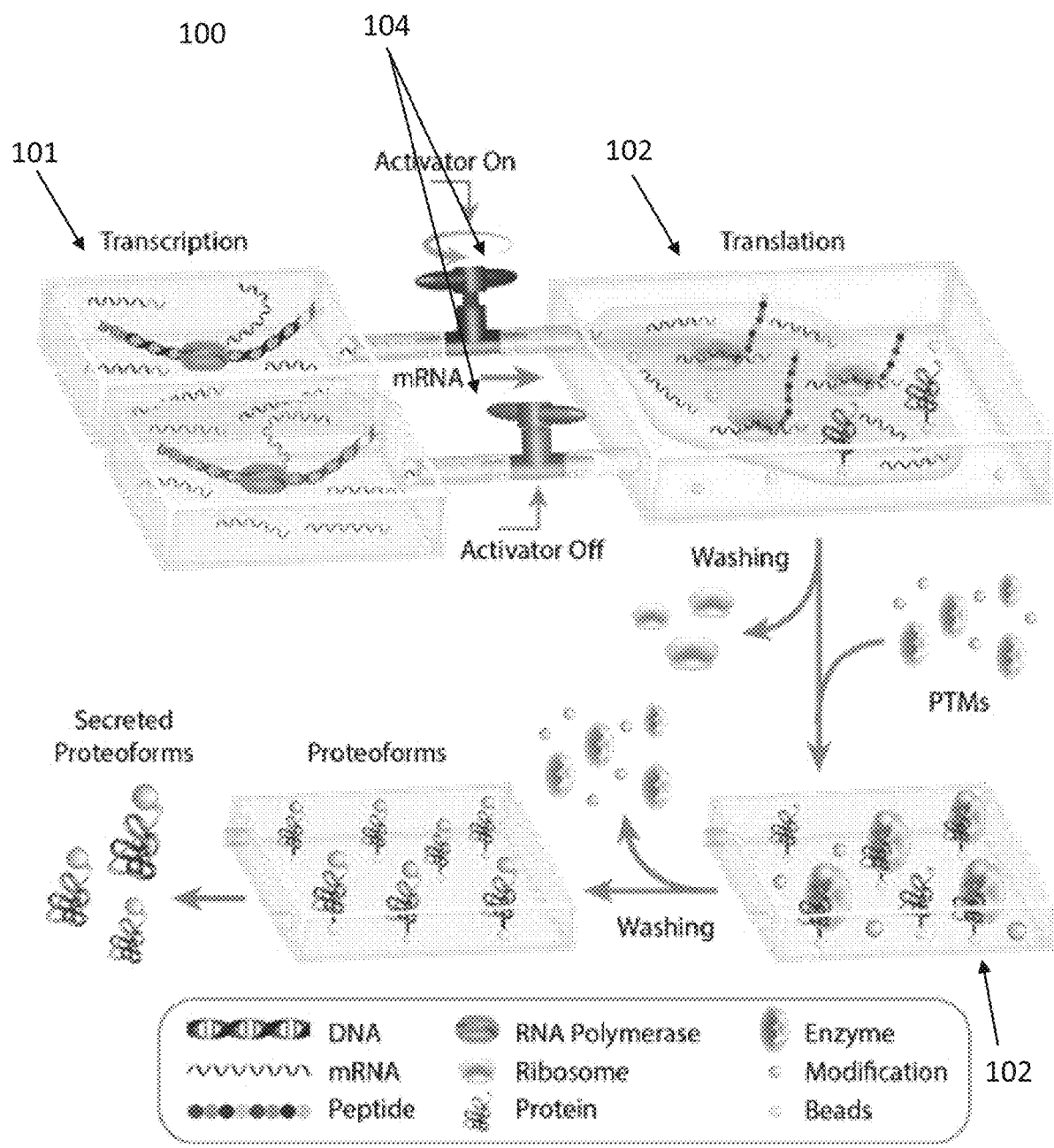
Figure 1C:
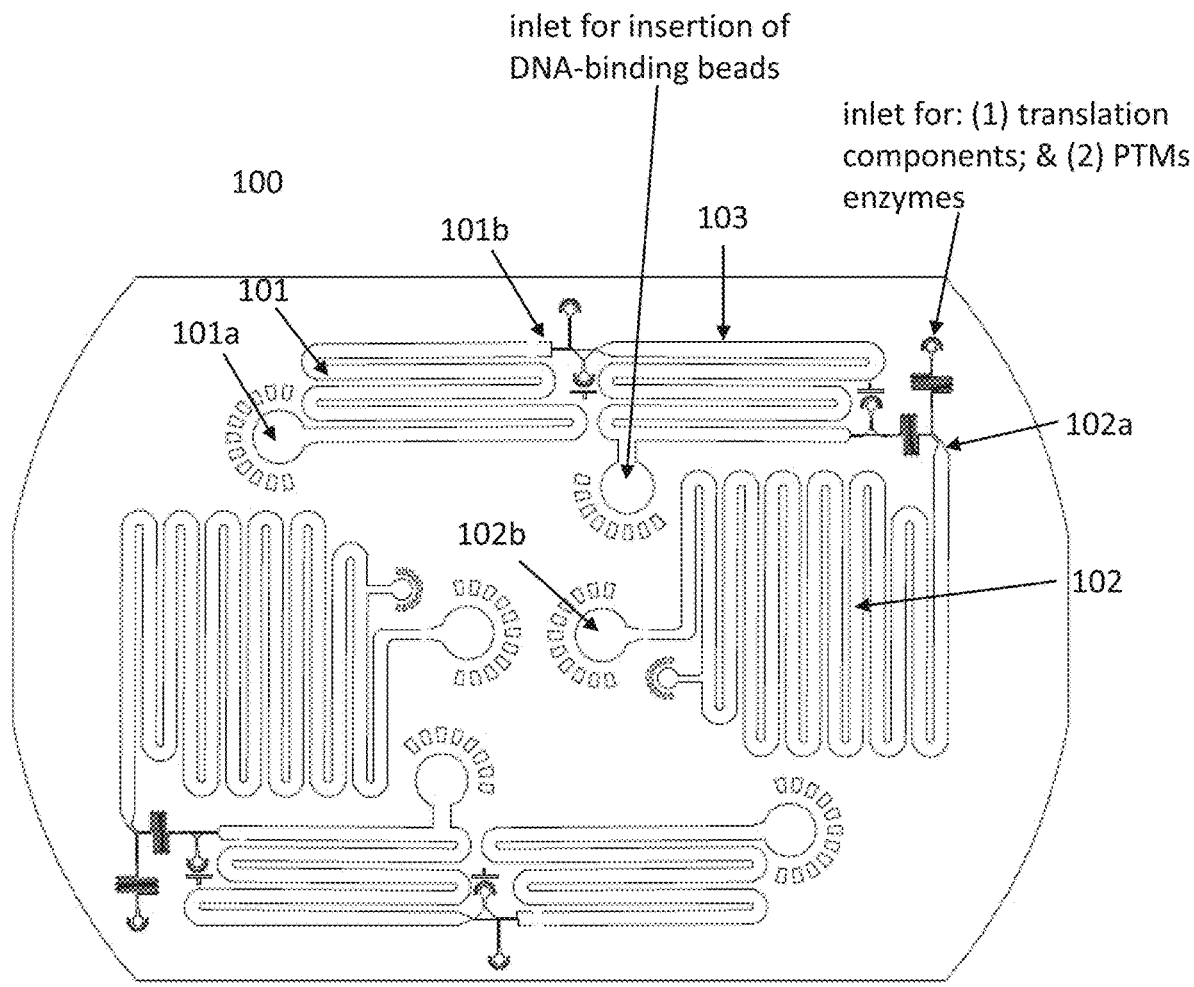
Figure 2A:
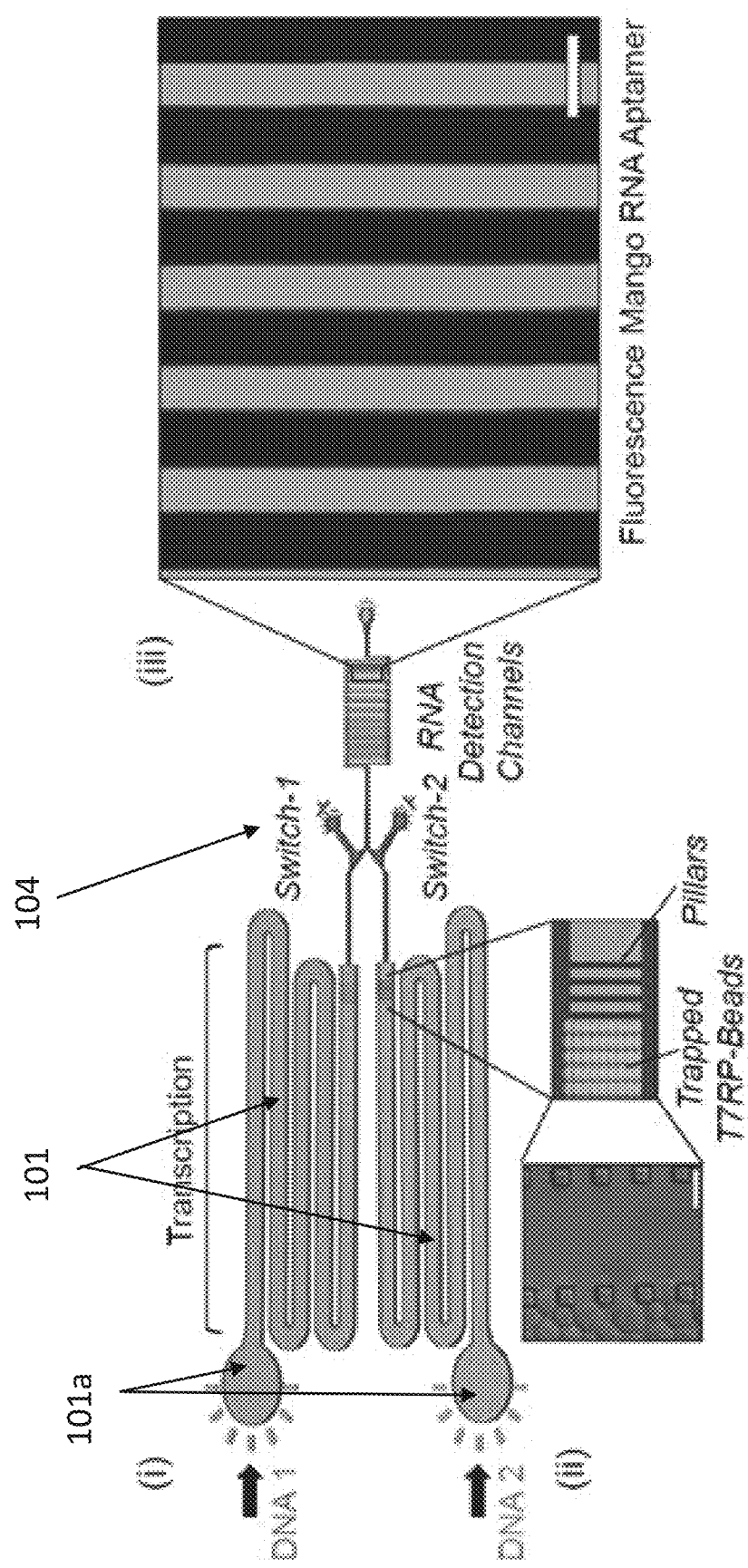
FIGS. 2A-2E show decoupling of transcription and translation by mechanical promotor-like valves.

To allow hierarchical implementation of transcription, translation and PTMs processes, we have utilized a microfluidics-based approach to reduce reagent usage and generate highly controlled micro-compartments comprising unique engineered features. In a CONTRALL biochip 100 as illustrated in FIGS. 1B & 1C, each process takes place within a different microcompartment 101,102 and the product is isolated or allowed to move into the subsequent compartment by a series of engineered microfluidic valves 104, used as ON/OFF switches, and size secluding pillars, which act as physical barriers for targeted molecules/elements (FIG. 2A).

Unless otherwise indicated, all numbers used in this specification are to be understood as being modified in all instances by the term "about". Accordingly, unless indicated to the contrary, the numerical parameters set forth in this specification are approximations that may vary by up to plus or minus 10% depending upon the desired properties to be obtained by the present invention.

The invention will now be illustrated by the following non-limiting Examples.

EXAMPLES

Materials and Methods
Biochip Preparation:
Biochip design: biochips were designed using AutoCAD software and consisted of either three compartments with connection channels and two valves for COmpartmentalized ceNTRal dogma activities Artificial ceLL (CONTRALL) platform (FIG. 3A) or two paralleled compartments with two valves and a detection channel (controlled mechanical promotor-like orthogonal valves) (FIG. 2A). All the compartments included four rows of pillars. Pillars dimensions were 25 μm×25 μm. In the CONTRALL biochip, the total channel length and width of either the first and second compartments (transcription and RNA transport) was ~85 mm and 1 mm, respectively. The third compartment (translation and PTMs) was ~222 mm in length and 1 mm in width. The height of the entire biochip was 50 μm. For the controlled mechanical promotor-like orthogonal valves biochip, each of the two parallel compartments was ~85 mm in length and 1 mm in width. Valve dimensions ranged from 1 to 1.5 cm in width, with a 17.5 mm distance between the valves and channels. Channels width was reduced to 13.5 mm.

Biochip fabrication: microfluidic CONTRALL biochips were fabricated from polydimethylsiloxane (PDMS, Dow Corning) using SU8 on silicon masters and standard soft lithography techniques. Inlets and outlets were punched and PDMS was then plasma bonded to glass slides to create a sealed biochip.

Beads Trapping on Biochip:

CONTRALL biochip (FIG. 3a): for transcription and translation compartments ($1^{st}$ and $3^{rd}$ compartments, respectively), high performance Ni beads (GE healthcare) were washed three times with ultra-pure water followed by three additional washes with the relevant buffer (transcription buffer; 200 mM Tris-HCl, 30 mM $MgCl_2$, 10 mM spermidine, 50 mM NaCl, 1 mM DTT pH 7.9. Translation buffer; Hepes-KOH pH 7.6). Following washes, the beads were inserted into the biochip. For the RNA purification compartment ($2^{nd}$ compartment), streptavidin resins (Genscript) were washed three times with transcription buffer and then inserted into the compartment.

Controlled mechanical promotor-like orthogonal valves biochip (FIG. 2a): high performance Ni beads (GE healthcare) were treated as outlined above and inserted into both compartments.

Immobilization of T7RP (FIGS. 2 and 3):

A plasmid encoding His-tagged T7RP was provided by Prof. Donald C. Rio (UC Berkeley). His-tagged T7RP was purified according to previously published protocols (A. Ciechanover et al., 2015). Following trapping of Ni beads in the transcription compartment 101, purified His-T7RP was flown at a rate of 100 μl $h^{-1}$ using Cetoni GmbH neMESYS Syringe Pumps (Korbussen, Germany), while the valve at the end of the compartment was open (2 mbar compressed air). The outlet at the end of the compartment allowed the removal of excess T7RP. The compartment was then washed with 100 μL transcription buffer at a rate of 800 μl $h^{-1}$. Following washes, the waste outlet was sealed with wax.

Transcription and RNA Purification (FIGS. 2 and 3):

Linear DNA fragments were produced by polymerase chain reaction (PCR) using Phusion High-Fidelity PCR Master Mix (NEB). For biotinylated products, PCR was carried out with one non-modified primer and another primer with biotin attached at the 5'-end (IDT). The biotin-conjugated primer was located downstream to the transcription terminator of all PCR products. PCR products were then purified using phenol:chloroform extraction. Transcription mix (transcription buffer with 500 ng PCR product) was flown into the transcription compartment, where T7RP was immobilized, at 100 μl $h^{-1}$ while the valve downstream to the compartment was open (2 mbar compressed air). The biochip was placed onto a 37° C. platform (NBT) for 1 hour. Following incubation, the valve was closed, allowing RNA transcripts alongside biotinylated DNA templates to flow downstream at a rate of 20 μl $h^{-1}$.

Translation (FIG. 3):

Following RNA transport, RNA transcripts were flown into the translation compartment at 20 μl $h^{-1}$. Simultaneously, Purefrex cell-free expression system solution (GeneFrontier) was flown from a separate inlet into the translation compartment at 20 μl $h^{-1}$. The biochip was then placed onto a 37° C. platform for 4 hours (NBT). Following translation, the compartment was washed with 500 μl of translation buffer at a rate of 800 μl $h^{-1}$. For His-eGFP assay, following the wash, 50 μl of elution buffer was used to elute His-eGFP at a flow rate of 800 μl $h^{-1}$.

Ubiquitination of In Vitro Translated and Immobilized His-Tagged α-Synuclein (FIG. 3):

His-tagged α-synuclein was translated and immobilized onto Ni beads in the translation compartment as described above. Following immobilization, the compartment was washed with 1× ubiquitin conjugation reaction buffer (Boston Biochem) at a rate of 800 μl $h^{-1}$. In vitro ubiquitination (IVU) reaction components were flown into the compartment (1 μM CHIP, 5 μM UbcH5b, 0.5 μM UbeI, 10 μM Ubiquitin, 1× ubiquitin conjugation reaction buffer, all from Boston Biochem) at a rate of 200 μl $h^{-1}$. The biochip was then placed onto a 37° C. platform for 0.5-3 hours (NBT). Following incubation, the compartment was washed with washing buffer (Phosphate saline buffer (PBS), 5 mM β-Mercaptoethanol, 10 mM Imidazole, pH 8.0) at a rate of 800 μl $h^{-1}$. 50 μl of elution buffer was then used at 800 μl $h^{-1}$ to elute His-tagged α-synuclein.

Figure 5:
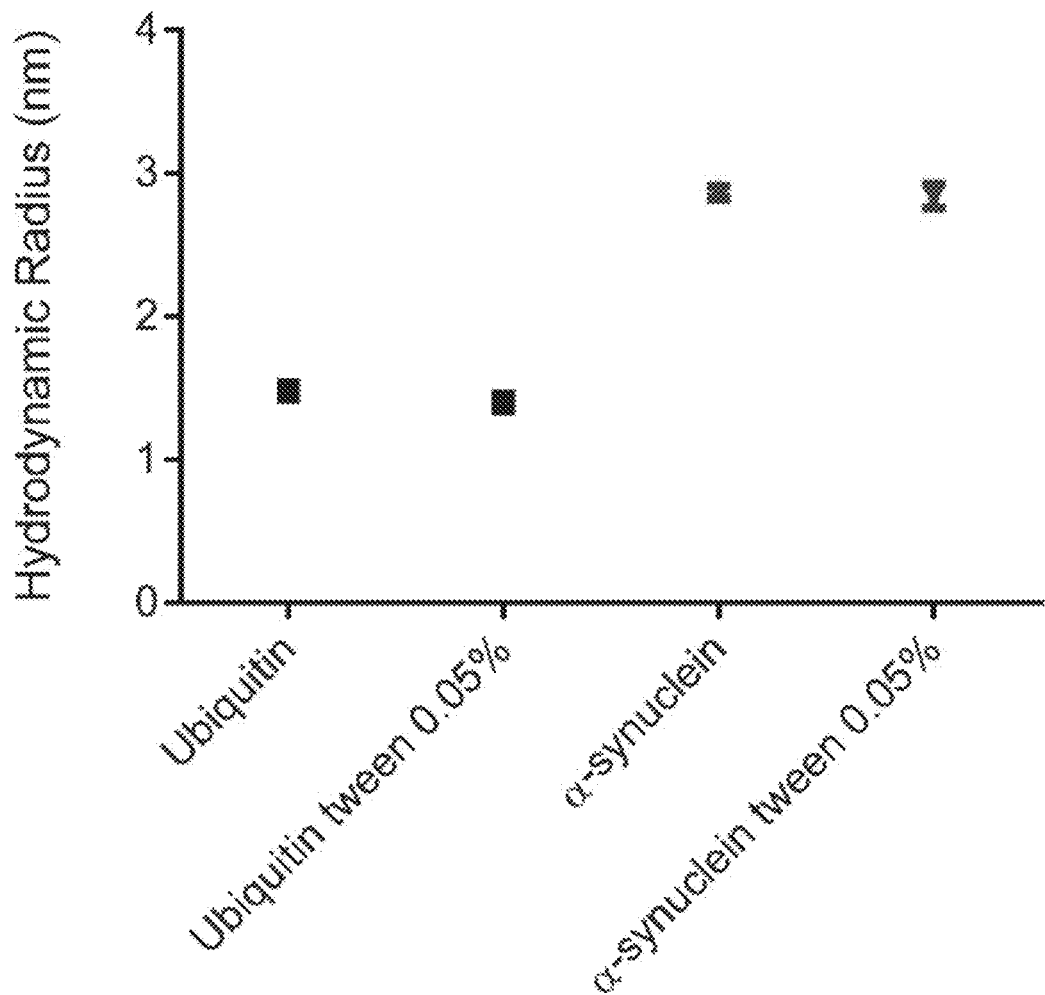
FIG. 5 show hydrodynamic radii of pure α-synuclein and ubiquitin compared to corresponding samples of α-synuclein and ubiquitin containing 0.05% Tween 20.
Figure 6:
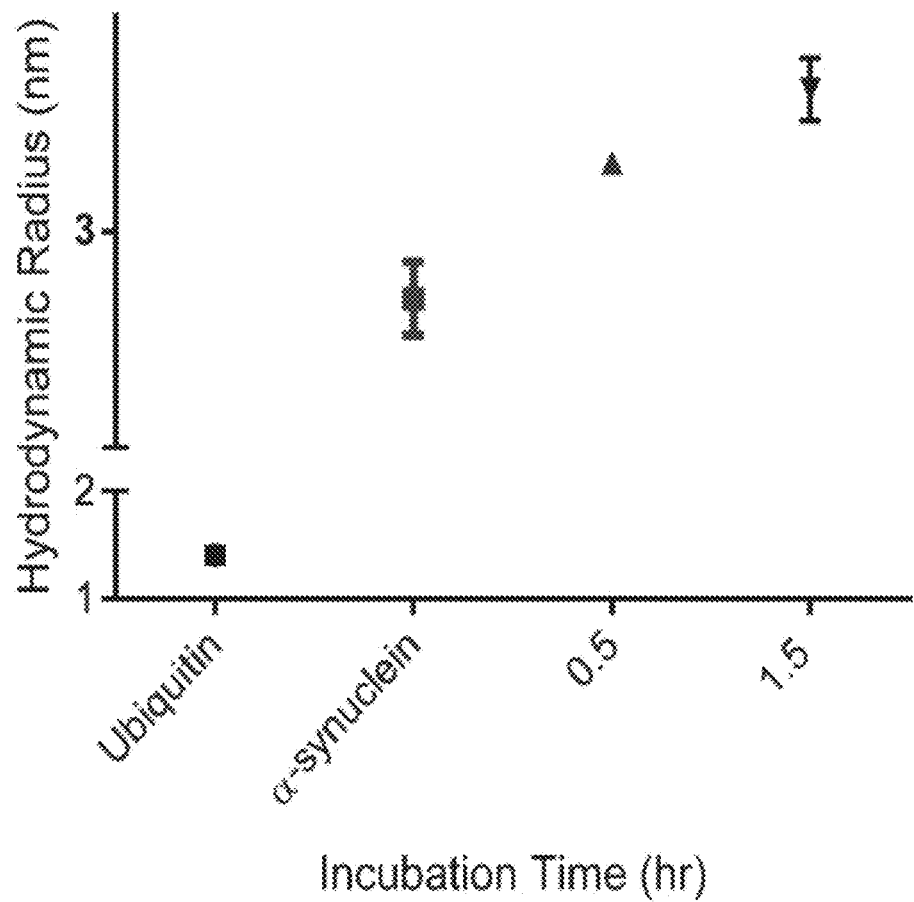
FIG. 6 is a graph showing diffusional sizing of ubiquitinated α-synuclein purified and modified by a biochip-system of the invention from *E. coli* (triangles) in comparison to pure ubiquitin and pure α-synuclein.
Figure 7:
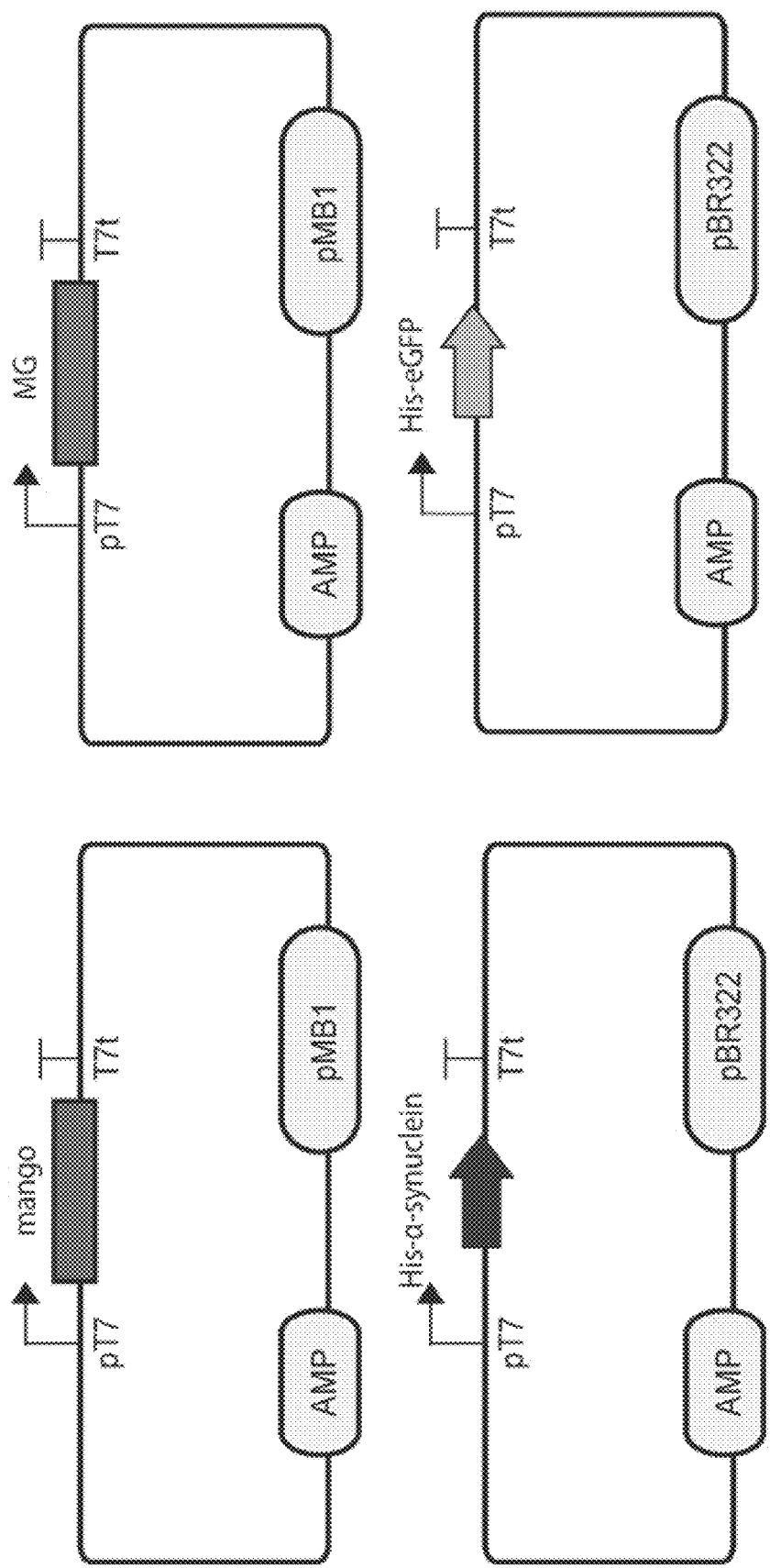
FIG. 7 shows maps of four plasmids that were used in the experiments shown in FIGS. 2 & 3. Partial sequences are provided in Table 1 below.

Hydrodynamic Radius Measurements of Ubiquitinated α-Synuclein (FIGS. 3e, 5 and 6):

De-salting and concentration of eluted modified α-synuclein were done using Amicon Ultra-0.5 mL Centrifugal Filters (Merk) according to the manufacturer's instructions. Tween 20 was added to the samples to a final concentration of 0.5%. A 5 μl sample was loaded onto Fluidity 1 chip (Fluidic Analytics).

Immunoblot (FIG. 3):

All samples were separated by 4-20% gradient SDS-PAGE (GeBA, Israel) and transferred onto polyvinylidene fluoride membrane using iBlot 2 Gel blotting system (Thermo Fisher Scientific). The membrane was then blocked for 1 hour in blocking solution (5% milk powder (Difco), 0.02% sodium-azide (Sigma-Aldrich) in 1×TTBS (0.1% Tween-20 in 1×TBS (Sigma-Aldrich)), and then incubated with the primary antibody diluted in blocking solution. The membrane was washed three times for 15 min each in TTBS, incubated for 1 hour in the secondary antibody and washed three times for 10 min each in TTBS. The membrane was developed using Clarity Western ECL (BIO-RAD), according to the manufacturer's instructions. Images were obtained using ChemiDoc touch Imaging System (BIO-RAD). For His-eGFP membrane, goat Anti-6×His tag antibody-ChIP grade primary antibody (Abcam) and Goat Anti-Rabbit IgG H&L (HRP) secondary antibody (Abcam) were used. For α-synuclein membranes, either Purified Mouse Anti-α-Synuclein primary antibody (BD) and Goat Anti-Mouse IgG H&L (HRP) secondary antibody (Abcam), or Anti-Ubiquitin antibody (Abcam) primary antibody and Goat Anti-Rabbit IgG H&L (HRP) secondary antibody (Abcam) were used.

Fluorescence Microscopy:

Mango light-up RNA aptamer (FIG. 2): Mango aptamer was transcribed in the transcription compartment of controlled mechanical promotor-like orthogonal valves biochip (as described above for transcription), while both valves were open (2 mbar compressed air) to prevent the transfer of the transcripts to the detection channel Following 1-hour incubation at 37° C., the valves were closed, and transcripts were flown into the detection channel at 100 µl h$^{-1}$.

His-eGFP bound to Ni beads (FIG. 3): His-eGFP was translated (as described above for transcription and translation). Images were obtained following flushing step for the removal of translation components.

In both cases, images were obtained using a Nikon Eclipse Ti-E inverted microscope with 470/40 excitation filter and 525/50 emission filter.

Fluorescence Measurements:

Transcription by immobilized T7RP (FIG. 2): T7RP was immobilized (as described above for transcription). Transcription mix containing either biotinylated DNA or non-biotinylated DNA encoding for mango light-up RNA aptamer or His-eGFP was added to the compartment. Following a 1-hour incubation at 37° C., the flow-through was collected and transferred into a 384-wells black plate (Greiner). Thiazol orange (Sigma Aldrich) was added to the samples to a final concentration of 5 nM. Excitation wavelength was 510 nm and fluorescence was measured at 535 nm using CLARIOstar plate reader (BMG LABTECH).

Oscillator switch (FIG. 2B): T7RP was immobilized as described above. Transcription mix containing malachite green (Sigma-Aldrich) at a final concentration of 50 µM and biotinylated DNA encoding for MG light-up RNA aptamer was added to one compartment (denoted compartment A). Transcription mix containing thiazol orange (Sigma-Aldrich) at a final concentration of 5 nM and biotinylated DNA encoding for mango light-up RNA aptamer was simultaneously added to the other compartment (denoted compartment B). Both transcription mix solutions were added while the valves were open (2 mbar compressed air) to prevent the transfer of the transcripts to the detection channel Following a 1-hour incubation at 37° C., compartment A valve was closed, allowing MG transcripts to flow to the downstream channel at a rate of 0.5 µl min$^{-1}$. The flow-through was then collected and transferred into a 384-wells black plate (Greiner) containing 19 µl of transcription buffer. Next, compartment A valve was opened, and compartment B valve was closed, allowing mango transcripts to flow at a rate of 0.5 µl min$^{-1}$. The flow-through was collected and transferred as described above. The valves alternations were repeated for a total of 14 times. Excitation wavelengths were 510 nm and 618 nm and emission was measured at 535 nm and 650 nm, respectively, using Tecan-Spark plate reader. Fluorescence signal of control samples (containing translation buffer and either thiazol orange at a final concentration of 5 nM or malachite green at a final concentration of 50 µM) were reduced from all measurements. The highest fluorescent signal measurement of each aptamer was set to 1 and all other measurements were normalized accordingly.

RNA accumulation of mango and MG light-up RNA aptamers (FIG. 2D): T7RP was immobilized as described above. Transcription mix containing malachite green (Sigma-Aldrich) at a final concentration of 50 µM and biotinylated DNA encoding for MG light-up RNA aptamer was added to one compartment (denoted compartment A). Transcription mix containing thiazol orange (Sigma-Aldrich) at a final concentration of 5 nM and biotinylated DNA encoding for mango light-up RNA aptamer was simultaneously added to the other compartment (denoted compartment B). Both transcription mix solutions were added while the valves were open (2 mbar compresses air) to prevent the transfer of the transcripts to the downstream detection channel. Following a one-hour incubation at 37° C., both valves were closed, allowing transcripts from both compartments to flow at 0.5 µl min$^{-1}$. Every 2 minutes, the flow-through was collected and transferred into a 96-wells black plate (Greiner) containing 200 µl of transcription buffer. Each collected fraction was added to the same well. Excitation wavelengths were 510 nm and 618 nm and emission was measured at 535 nm and 650 nm, respectively, using Tecan-Spark plate reader. Fluorescence signal was then normalized as previously described for the oscillator assay.

RNA accumulation of mango light-up RNA aptamer (FIG. 2D): This experiment was performed as described above for RNA accumulation of mango and MG light-up RNA aptamers (FIG. 2), except mango light-up RNA aptamer was transcribed in both parallel compartments.

DNA Constructs:

All DNA sequences are provided in Table 1 below. Plasmid encoding for mango light-up RNA aptamer was purchased from Genscript. All other plasmids were constructed using Gibson Assembly Master Mix (NEB) according to standard Gibson assembly method (D. C. Gibson et al., 2009; S. Zilberzwige-Tal et al., 2018).

TABLE 1

| Part | Sequence | Seq ID NO: |
|---|---|---|
| T7 promotor | TAATACGACTCACTATAG | 1 |
| T7 terminator | CTAGCATAACCCCTTGGGGCCTCTAAACGGGTCTTGAG GGGTTTTTG | 2 |
| Mango aptamer | GGATGCGTAACCCTCAAGGAACCCGCAAGCCATCGGGA CTCAAGCCGCCGGTACCTCCGAAGGGACGGTGCGGAGA GGAGAGGGGGCACTGGGCGGCTGTGTGAGATTCTGCCA AATAGACAGCCGAA | 3 |
| MG aptamer | GGATCCCGACTGGCGAGAGCCAGGTAACGAATGGATCC | 4 |
| His-tagged eGFP | ATGGGCAGCAGCCATCATCATCATCATCACAGCAGCGG CCTGGTGCCGCGCGGCAGCCATATGGTGAGCAAGGGCG AGGAGCTGTTCACCGGGGTGGTGCCCATCCTGGTCGAG CTGGACGGCGACGTAAACGGCCACAAGTTCAGCGTGTC CGGCGAGGGCGAGGGCGATGCCACCTACGGCAAGCTGA CCCTGAAGTTCATCTGCACCACCGGCAAGCTGCCCGTG CCCTGGCCCACCCTCGTGACCACCCTGACCTACGGCGT GCAGTGCTTCAGCCGCTACCCCGACCACATGAAGCAGC ACGACTTCTTCAAGTCCGCCATGCCCGAAGGCTACGTC CAGGAGCGCACCATCTTCTTCAAGGACGACGGCAACTA CAAGACCCGCGCCGAGGTGAAGTTCGAGGGCGACACCC TGGTGAACCGCATCGAGCTGAAGGGCATCGACTTCAAG GAGGACGGCAACATCCTGGGGCACAAGCTGGAGTACAA CTACAACAGCCACAACGTCTATATCATGGCCGACAAGC AGAAGAACGGCATCAAGGTGAACTTCAAGATCCGCCAC AACATCGAGGACGGCAGCGTGCAGCTCGCCGACCACTA CCAGCAGAACACCCCCATCGGCGACGGCCCCGTGCTGC TGCCCGACAACCACTACCTGAGCACCCAGTCCGCCCTG AGCAAAGACCCCAACGAGAAGCGCGATCACATGGTCCT GCTGGAGTTCGTGACCGCCGCCGGGATCACTCTCGGCA TGGACGAGCTGTAG | 5 |
| His-tagged α-synuclein | ATGGGCAGCAGCCATCATCATCATCATCACAGCAGCGG CCTGGTGCCGCGCGGCAGCCATATGGATGTATTCATGA AAGGACTTTCAAAGGCCAAGGAGGGAGTTGTGGCTGCT GCTGAGAAAACCAAACAGGGTGTGGCAGAAGCAGCAGG AAAGACAAAAGAGGGTGTTCTCTATGTAGGCTCCAAAA CCAAGGAGGGAGTGGTGCATGGTGTGGCAACAGTGGCT GAGAAGACCAAAGAGCAAGTGACAAATGTTGGAGGAGC AGTGGTGACGGGTGTGACAGCAGTAGCCCAGAAGACAG TGGAGGGAGCAGGGAGCATTGCAGCAGCCACTGGCTTT GTCAAAAAGGACCAGTTGGGCAAGAATGAAGAAGGAGC CCCACAGGAAGGAATTCTGGAAGATATGCCTGTGGATC | 6 |

TABLE 1-continued

| Part | Sequence | Seq ID NO: |
|------|----------|------------|
| | CTGACAATGAGGCTTATGAAATGCCTTCTGAGGAAGGG TATCAAGACTACGAACCTGAAGCCTAG | 5 |

Mass Spectrometry:

Ubiquitinated α-synuclein was produced as described previously. The samples were subjected to in-solution tryptic digestion, followed by a desalting step. The resulting peptides were analyzed using nanoflow liquid chromatography (nanoAcquity) coupled to high resolution, high mass accuracy mass spectrometry (Q Exactive Plus). The data was processed using Byonic search engine (Protein Metrics Inc) using the Human proteome database concatenated with common contaminants, using the following modifications—fixed carbamidomethylation on C, oxidation on M, deamidation on NQ, pyro Glu on N-terminal NQ, GlyGly on K and acetylation on protein N-terminus. The results were screened manually to verify identified K ubiquitination sites (D. C. Rio, et al., 2013).

EXPERIMENTAL EXAMPLES

Example 1

Decoupling Transcription from Translation

Figure 2B:
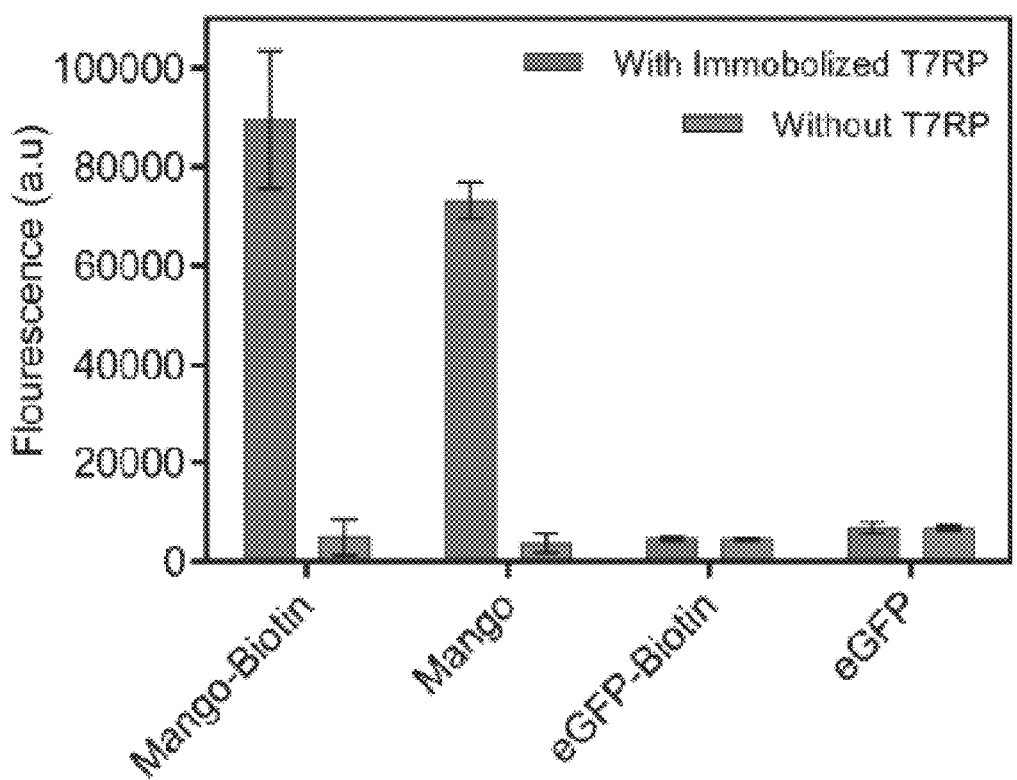
Figure 2C:
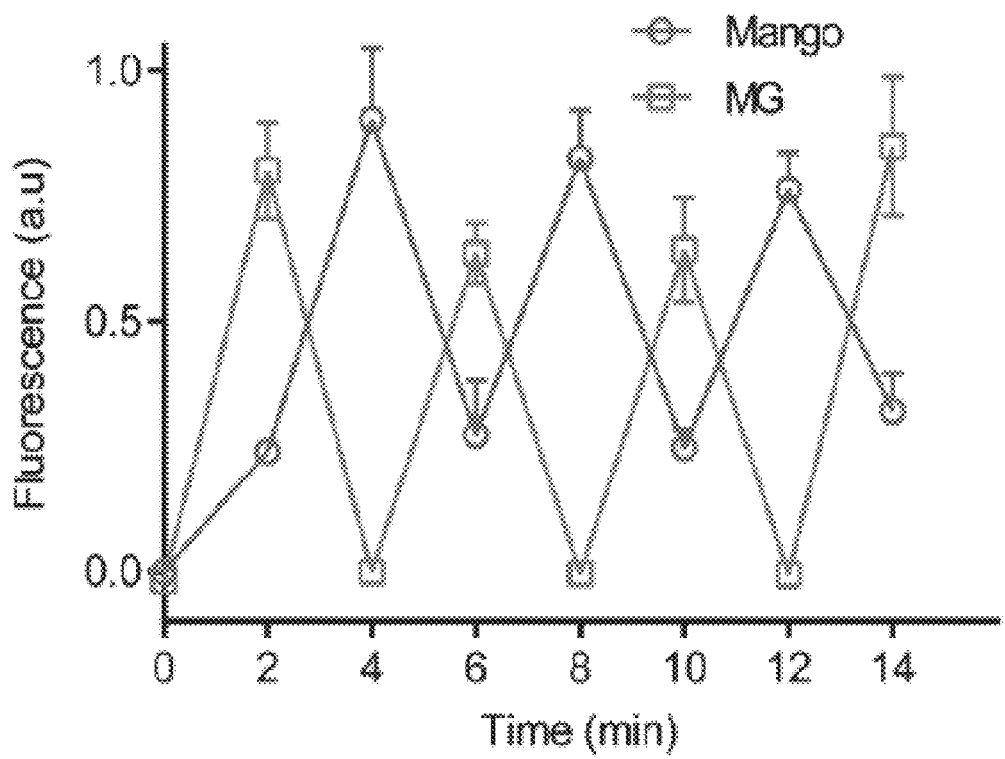
Figure 2D:
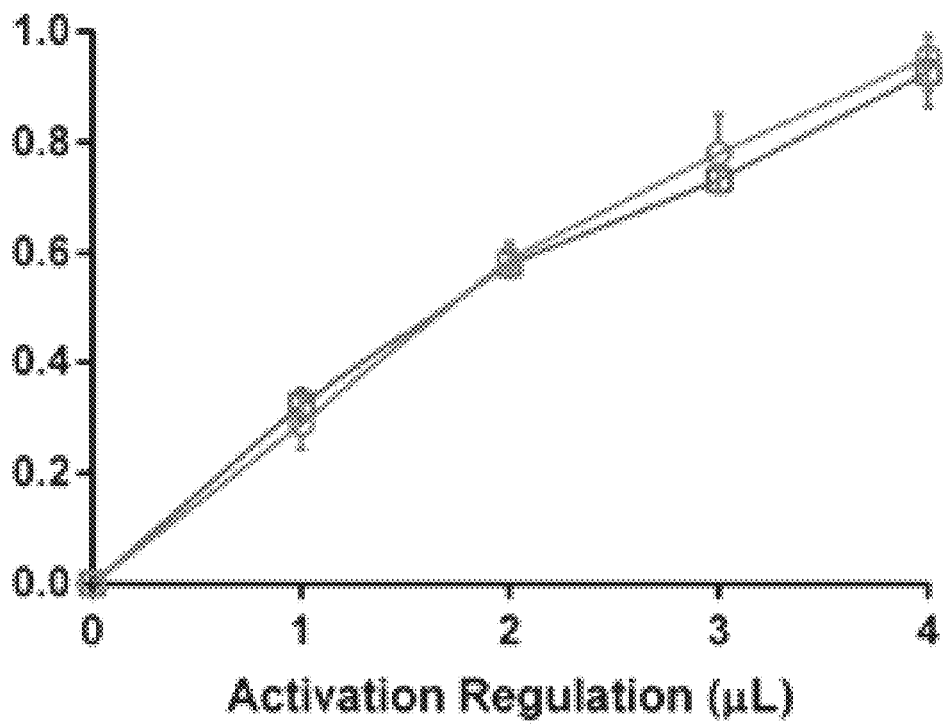
Figure 2E:
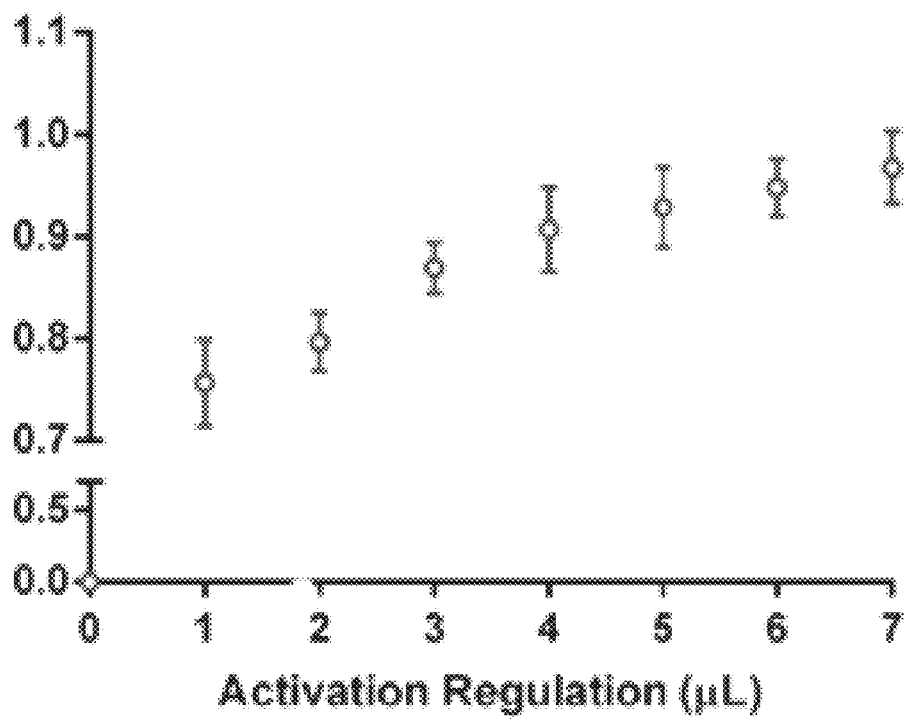

First, aiming to recapitulate the natural eukaryotic cell process, we sought to decouple transcription from translation (S. R. Wente et al., 2010). A biochip comprising two confined parallel transcription compartments 101 with a set of controlled mechanical promotor-like valves (FIG. 2A) was developed, thereby allowing control of transcription initiation and strength. The compartments 101 were followed by a detection channel where mango RNA could be detected. To localize and segregate transcription in a confined environment, PDMS-based lithographically defined molecules/elements was used to trap Ni beads bound to His-tagged T7 RNA polymerase (T7RP), thereby immobilizing the enzyme and preventing its transfer to downstream compartments (FIGS. 2A and 4A-4D). To verify sufficiently effective and accurate transcription by the immobilized T7RP, we employed the biochip to transcribe mango light-up RNA aptamer, which generates a fluorescent signal only in the presence of a specific fluorogene when its secondary structure remains active (F. Bouhedda et al., 2017). Following transcription, it was possible to detect a fluorescent signal from the reaction flow-through, demonstrating correct transcription by immobilized T7RP (FIG. 2B). Expanding on this approach, we have been able to transcribe two different RNA light-up aptamers in two parallel compartments. By alternatively modulating the flow rate and valve shuttering of the two compartments, we developed an oscillator switch of RNA transcripts (FIG. 2C). By selectively transferring different volumes of the RNA transcript solution, we demonstrated the controlled accumulation of specific RNA transcripts in the collected fraction, thus mimicking mechanically promotor strength (FIG. 2D). The immobilization of T7RP holds great potential for re-using the transcription compartment with different genes.

Figure 3A:
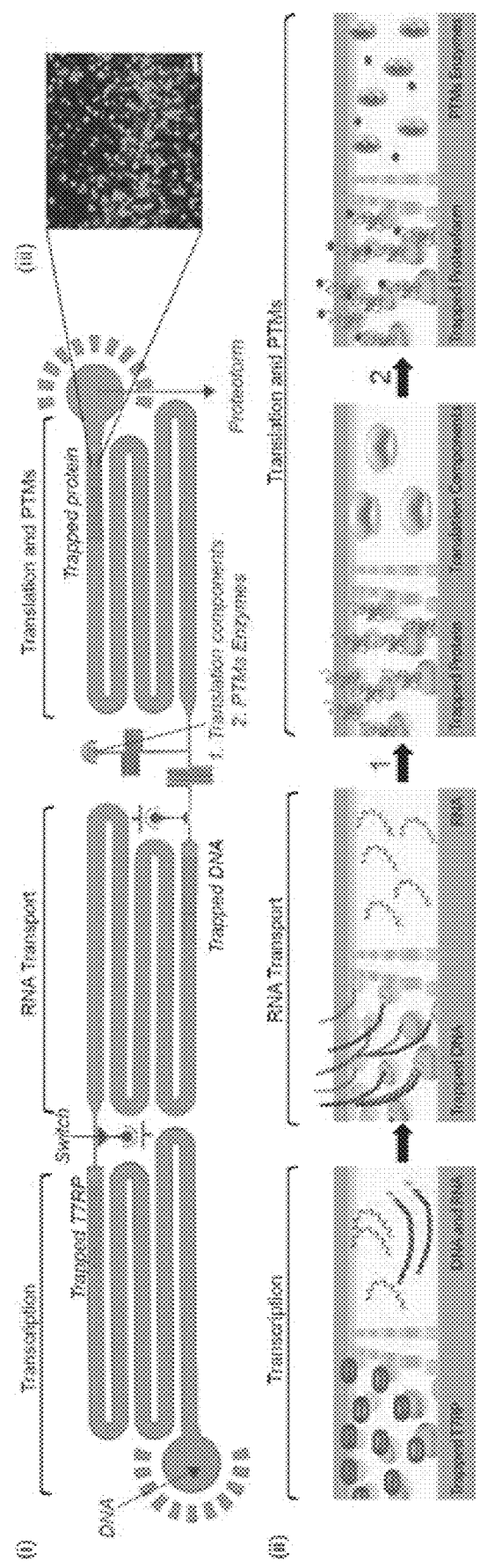
FIGS. 3A-3F depict translation and characterization of purified His-eGFP and α-synuclein proteoforms.

Following the establishment of confined and controlled transcription processes, we aimed to mimic nuclear transport, a key feature in all eukaryotic cells, comprising the tightly regulated and highly selective mobilization of RNA transcripts from the nucleus to the cytoplasm (S. R. Wente et al., 2010). First, we verified the ability of the immobilized T7RP to transcribe from both biotinylated and non-modified-DNA template molecules (FIG. 2B). Following transcription, the solution containing RNA molecules, biotinylated DNA and other essential components was flown into a downstream channel comprised of immobilized streptavidin (SA) beads, which bound the biotinylated DNA and allowed RNA transcripts to continue flowing into the translation compartment (FIG. 3A).

Example 2

Translation

Figure 3B:
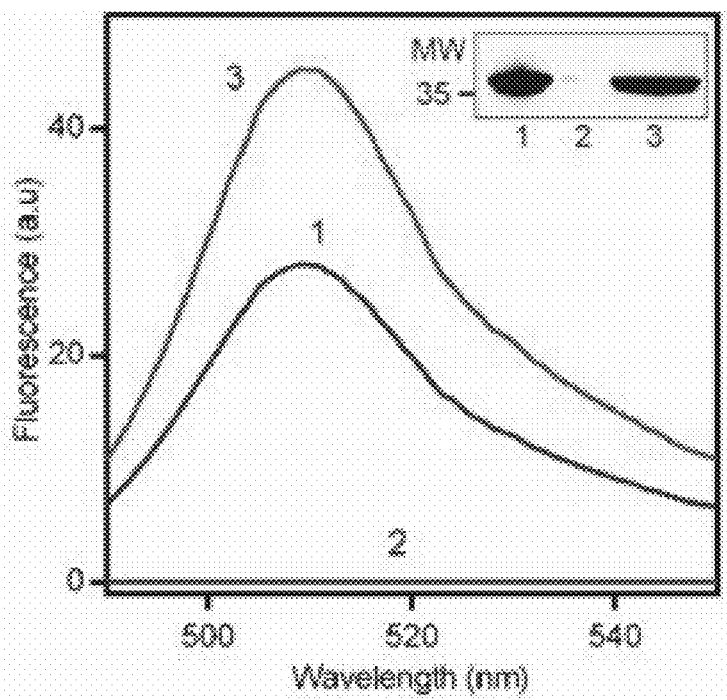
Figure 3F:
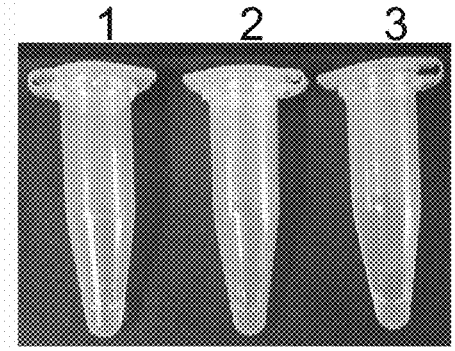
Figure 3C:
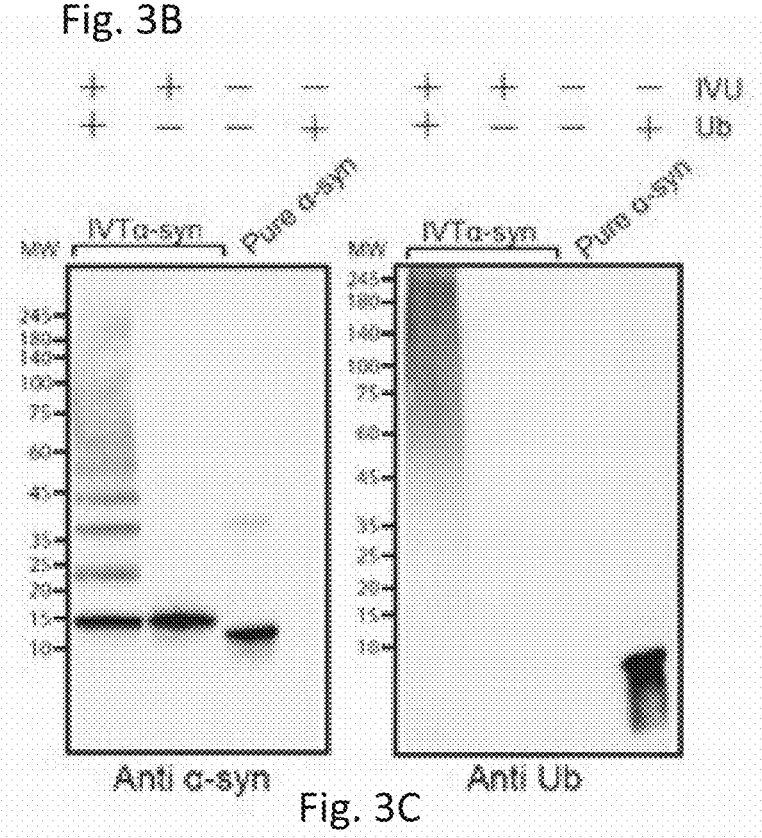

To avoid introducing additional background noise during the translation process, we used cell-free protein synthesis kit, PUREfrex, which comprises untagged purified translation machinery components of E. coli with reduced contaminations 19 (Y. Shimizu et al., 2014). These components were directly introduced into the translation compartment via an inlet (FIG. 3A). Following transcription and RNA mobilization into the translation compartment, RNA molecules encoding His-tagged Green Fluorescent Protein (eGFP) encountered the PUREfrex components, facilitating the translation process. The newly translated His-eGFP was immobilized using Ni beads trapped inside the compartment. Following translation, the compartment was washed to remove any remaining RNA molecules and translation components, while the His-eGFP remained trapped. His-eGFP was then eluted from the CONTRALL biochip using an imidazole-based solution. Using fluorescence spectrum and Western blot analysis His-eGFP was detected in both the translation and elution solutions, but not in the flow-through fraction, indicated that most of the translated protein was trapped within the CONTRALL biochip (FIGS. 3B, 3C and 3F). The CONTRALL protein yield is ~24 μg/mL per cycle.

Example 3

Post-Translational Modification

After establishing the ability to both translate and immobilize a protein of choice in a controlled environment, we proceeded to perform site-specific PTMs by enzymatic means. PTMs allow to further extend the functionality of proteins by yielding a wide range of protein variants consisting of the same amino acid sequences. Implementing PTMs compartment as part of the CONTRALL platform will potentially allow producing different proteins caring various PTMs. As a model protein, we used α-synuclein, a natively unfolded protein, shown to be linked to Parkinson's disease (T. M. Dawson et al., 2003). Understanding the molecular mechanisms underlying α-synuclein aggregation and identifying α-synuclein's modification sites could result in more effective therapeutic strategies. α-synuclein has been shown to be mono- and poly-ubiquitinated by the E3 ubiquitin ligase, Hsp70-interacting protein (CHIP) (L. V. Kalia et al., 2011). CHIP E3 ligase was shown to reduce α-synuclein oligomerization and mediate the degradation of misfolded proteins associated with Alzheimer disease, Huntington and Parkinson's disease (A. Ciechanover et al., 2015). However, the ubiquitination sites in which CHIP E3 ubiquitinates α-synuclein have not been identified to date (L. V. Kalia et al., 2011; A. Ciechanover et al., 2015). Understanding the molecular mechanisms underlying α-synuclein aggregation and identifying α-synuclein's ubiquitination sites could results in more effective therapeutic strategies.

Figures 3D, 3E:
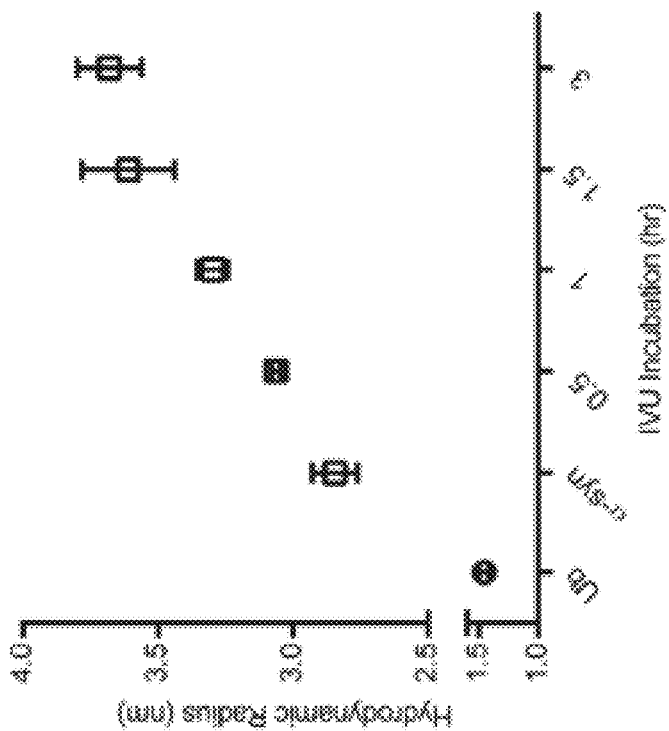

Here, His-α-synuclein was translated and immobilized onto Ni beads in the translation compartment of the CONTRALL biochip as detailed above. Following a washing step, we introduced in vitro ubiquitination components including CHIP E3 ligase. Following increased incubation times, the compartment was washed, yielding purified immobilized α-synuclein, which was eluted in a similar manner to His-eGFP. To validate the formation of ubiquitinated α-synuclein, Western blot analysis was applied, indicating that the newly formed α-synuclein proteoforms were both mono- and poly-ubiquitinated (FIG. 3C). Using mass spectrometry, we were able to identify, for the first time, the CHIP E3 ligase ubiquitination sites on α-synuclein proteoforms (FIG. 3D). In parallel, microfluidic diffusional sizing was used to determine directly in the solution state under native conditions the average hydrodynamic radius of the resulting ubiquitinated α-synuclein. The results demonstrate a time-dependent increase in the hydrodynamic radius of the ubiquitinated α-synuclein, compared to pure ubiquitin or α-synuclein (FIG. 3E), directly reporting on the increased ubiquitination over time.

REFERENCES

A. Ciechanover, Y. T. Kwon, *Exp Mol Med* 2015, 47, e147.
B. A. Garcia, S. B. Hake, R. L. Diaz, M. Kauer, S. A. Morris, J. Recht, J. Shabanowitz, N. Mishra, B. D. Strahl, C. D. Allis, D. F. Hunt, *J Biol Chem* 2007, 282, 7641-7655.
D. C. Rio, *Cold Spring Harb Protoc* 2013, 2013.
D. G. Gibson, L. Young, R. Y. Chuang, J. C. Venter, C. A. Hutchison, 3rd, H. O. Smith, *Nat Methods* 2009, 6, 343-345.E. Karzbrun, A. M. Tayar, V. Noireaux, R. H. Bar-Ziv, *Science* 2014, 345, 829-832.
F. Bouhedda, A. Autour, M. Ryckelynck, *Int J Mol Sci* 2017, 19.
F. Katzen, G. Chang, W. Kudlicki, *Trends Biotechnol* 2005, 23, 150-156.
J. Garamella, R. Marshall, M. Rustad, V. Noireaux, *ACS Synth Biol* 2016, 5, 344-355.
K. L. Kim, K. M. Park, J. Murray, K. Kim, S. H. Ryu, *ACS Cent Sci* 2018, 4, 614-623.
K. Pardee, A. A. Green, T. Ferrante, D. E. Cameron, A. DaleyKeyser, P. Yin, J. J. Collins, *Cell* 2014, 159, 940-954.
L. Aufinger, F. C. Simmel, *Angew Chem Int Ed Engl* 2018.
L. V. Kalia, S. K. Kalia, H. Chau, A. M. Lozano, B. T. Hyman, P. J. McLean, *PLoS One* 2011, 6, e14695.
M. C. Jewett, B. R. Fritz, L. E. Timmerman, G. M. Church, *Mol Syst Biol* 2013, 9, 678.
M. J. Smanski, H. Zhou, J. Claesen, B. Shen, M. A. Fischbach, C. A. Voigt, *Nat Rev Microbiol* 2016, 14, 135-149.
M. Pfammatter, M. Andreasen, G. Meisl, C. G. Taylor, J. Adamcik, S. Bolisetty, A. Sanchez-Ferrer, D. Klenerman, C. M. Dobson, R. Mezzenga, T. P. J. Knowles, A. Aguzzi, S. Hornemann, *Anal Chem* 2017, 89, 12306-12313.
M. W. Nirenberg, J. H. Matthaei, *Proc Natl Acad Sci USA* 1961, 47, 1588-1602.
P. Arosio, T. Muller, L. Rajah, E. V. Yates, F. A. Aprile, Y. Zhang, S. I. Cohen, D. A. White, T. W. Herling, E. J. De Genst, S. Linse, M. Vendruscolo, C. M. Dobson, T. P. Knowles, *ACS Nano* 2016, 10, 333-341.
Q. M. Dudley, A. S. Karim, M. C. Jewett, *Biotechnol J* 2015, 10, 69-82.
S. J. Moore, J. T. MacDonald, S. Wienecke, A. Ishwarbhai, A. Tsipa, R. Aw, N. Kylilis, D. J. Bell, D. W. McClymont, K. Jensen, K. M. Polizzi, R. Biedendieck, P. S. Freemont, *Proc Natl Acad Sci USA* 2018, 115, E4340-E4349.
S. R. Wente, M. P. Rout, *Cold Spring Harb Perspect Biol* 2010, 2, a000562.
S. Zilberzwige-Tal, E. Gazit, *Chemistry, an Asian journal* 2018, 13, 3437-3447.
Saggio and Laufer, *Biochem. J.* 1993, 293, 613-616.
T. M. Dawson, V. L. Dawson, *Science* 2003, 302, 819-822.
T. Trantidou, M. Friddin, Y. Elani, N. J. Brooks, R. V. Law, J. M. Seddon, O. Ces, *ACS Nano* 2017, 11, 6549-6565.
V. Noireaux, A. Libchaber, *Proc Natl Acad Sci USA* 2004, 101, 17669-17674.
W. Kightlinger, L. Lin, M. Rosztoczy, W. Li, M. P. DeLisa, M. Mrksich, M. C. Jewett, *Nat Chem Biol* 2018, 14, 627-635.
Y. Heyman, A. Buxboim, S. G. Wolf, S. S. Daube, R. H. Bar-Ziv, *Nat Nanotechnol* 2012, 7, 374-378.
Y. Iwane, A. Hitomi, H. Murakami, T. Katoh, Y. Goto, H. Suga, *Nat Chem* 2016, 8, 317-325.
Y. Shimizu, Y. Kuruma, T. Kanamori, T. Ueda, *Methods Mol Biol* 2014, 1118, 275-284.

The invention claimed is:

1. A cell-free system (100) comprising:
(i) a transcription compartment (101) for DNA transcription, designed to bind an RNA polymerase or retain microbeads capable of binding an RNA polymerase, said compartment (101) comprises a fluid inlet port (101*a*) and a fluid outlet port (101*b*);
(ii) a barrier for selectively preventing or substantially decreasing passage of DNA or modified-DNA therethrough, wherein said barrier is designed to bind a molecule capable of selectively binding DNA or modified-DNA, or retain microbeads capable of binding said molecule, and said barrier is fluidly connected to or comprised within said compartment (101); and
(iii) a translation compartment (102) for translation of mRNA to protein and optionally posttranslational modification (PTM) of said protein, said compartment (102) comprises a fluid inlet port 102*a* (102*a*) that is fluidly connected to said outlet port (101*b*) or said barrier, and a fluid outlet port 102*b* (102*b*), wherein said compartment (102) is designed to bind said protein or retain microbeads capable of binding said protein, wherein:
(a) an inner surface of said transcription compartment (101) comprises a first functional group of a specific binding pair capable of binding to a complementary second functional group of said binding pair present on said RNA polymerase, and is therefore designed to bind to said RNA polymerase; or
(b) said transcription compartment (101) comprises a physical obstacle designed to prevent passage of said microbeads, if present, therethrough, and therefore retain said RNA polymerase bound to said microbeads.

2. The cell-free system (100) of claim 1, wherein said barrier comprises a
molecule capable of selectively binding DNA or modified-DNA, or is designed to retain microbeads comprising or capable of binding said molecule.

3. The cell-free system (100) of claim 1, wherein said compartment (101) comprises a physical obstacle designed to prevent passage of microbeads capable of binding said RNA polymerase therethrough, and said physical obstacle comprises multiple pillars, each one of which is separated from an adjacent pillar or inner surface of said compartment (101) by a space that is smaller than the microbeads' diameter.

4. The cell-free system (100) of claim 3, wherein said compartment (101) comprises microbeads bound to or designed to bind said RNA polymerase.

5. The cell-free system (100) of claim 3, wherein said compartment (101) lacks microbeads bound to or designed to bind said RNA polymerase.

6. The cell-free system (100) of claim 3, wherein said microbeads comprise a transition metal ion having high affinity to poly-histidine sequence (His-tag); and said RNA polymerase comprises a His-tag bound to said transition metal ion.

7. The cell-free system (100) of claim 6, wherein said transition metal ion
is selected from the group consisting of $Ni^{2+}$, $Co^{2+}$, $Cu^{2+}$, and $Zn^{2+}$.

8. The cell-free system (100) of claim 1, comprising:
(i) a transcription compartment (101) for DNA transcription, retaining or designed to retain microbeads capable of binding an RNA polymerase, said compartment (101) comprising a fluid inlet port (101*a*) through which DNA and optionally the RNA polymerase are inserted; a fluid outlet port (101*b*) through which mRNA exits; and a physical obstacle designed to prevent passage of microbeads capable of binding the RNA polymerase, wherein said physical obstacle comprising multiple pillars, each one of which is separated from an adjacent pillar or inner surface of the compartment (101) by a space that is smaller than the microbeads' diameter;
(ii) a barrier for selectively preventing or substantially decreasing passage of DNA or modified-DNA therethrough, wherein said barrier is designed to bind a molecule capable of selectively binding DNA or modified-DNA, or retain microbeads capable of binding said molecule, and said barrier is fluidly connected to or comprised within said compartment (101); and
(iii) a translation compartment (102) for translation of mRNA to protein and optionally for post-translational modification (PTM) of the protein, the compartment (102) comprises a fluid inlet port (102*a*) that is fluidly connected to the outlet port (101*b*) or the barrier, and a fluid outlet port (102*b*), wherein the compartment (102) is designed to bind the protein or retain micro beads capable of binding the protein.

9. The cell-free system (100) of claim 1, wherein said inner surface of said compartment (101) comprises a first functional group of a specific binding pair capable of binding to a complementary second functional group of said binding pair present on said RNA polymerase.

10. The cell-free system (100) of claim 9, wherein said compartment (101) comprises said RNA polymerase linked to said first functional group via said second functional group.

11. The cell-free system (100) of claim 1, comprising:
(i) a transcription compartment (101) for DNA transcription, designed to bind an RNA polymerase, said compartment (101) comprising a fluid inlet port (101*a*) through which DNA and optionally the RNA polymerase are inserted; a fluid outlet port (101*b*) through which m RNA exits; and a first functional group of a specific binding par capable of binding to a complementary second functional group of said binding pair present on said RNA polymerase
(ii) a barrier for selectively preventing or substantially decreasing passage of DNA or modified-DNA therethrough, wherein said barrier is designed to bind a molecule capable of selectively binding DNA or modified-DNA, or retain microbeads capable of binding said molecule, and said barrier is fluidly connected to or comprised within said compartment (101); and
(iii) a translation compartment (102) for translation of mRNA to protein and optionally for post-translational modification (PTM) of the protein, the compartment (102) comprises a fluid inlet port (102*a*) that is fluidly connected to the outlet port (101*b*) or the barrier, and a fluid outlet port (102*b*), wherein the compartment (102) is designed to bind the protein or retain micro beads capable of binding the protein.

12. The cell-free system (100) of claim 1, wherein said barrier comprises
a physical obstacle designed to prevent passage of microbeads capable of selectively binding DNA or modified-DNA, and is localized in a physical compartment (103) spatially separated from but fluidly connected to said compartment (101) and to said compartment 402 (102).

13. The cell-free system 100 of claim 12, wherein said compartment 103 further comprises said microbeads.

14. The cell-free system 100 of claim 13, wherein said microbeads are bound to a molecule capable of selectively binding DNA or modified-DNA.

15. A cell-free system (100) comprising:
(i) a transcription compartment (101) for DNA transcription, designed to bind an RNA polymerase or retain microbeads capable of binding an RNA polymerase, said compartment (101) comprises a fluid inlet port (101*a*) and a fluid outlet port (101*b*);
(ii) a translation compartment (102) for translation of mRNA to protein and optionally for PTM of said protein, said compartment (102) comprises a fluid inlet port (102*a*) that is fluidly connected to said outlet port (101*b*) or a barrier, and a fluid outlet port (102*b*), wherein said compartment (102) is designed to bind said protein or retain microbeads capable of binding said protein; and
(iii) a barrier compartment (103) spatially separated from but fluidly connected to said compartment (101) and said compartment (102) for selectively preventing or substantially decreasing passage of DNA or modified-DNA therethrough, wherein said barrier compartment (103) is designed to bind a molecule capable of selectively binding DNA or modified-DNA, or retain microbeads capable of binding said molecule,
wherein:
(a) an inner surface of said transcription compartment (101) comprises a first functional group of a specific binding pair capable of binding to a complementary second functional group of said binding pair present on said RNA polymerase, and is therefore designed to bind to said RNA polymerase; or
(b) said transcription compartment (101) comprises a physical obstacle designed to prevent passage of said microbeads, if present, therethrough, and therefore retain said RNA polymerase bound to said microbeads.

16. The cell-free system (100) of claim 12, wherein said physical obstacle
comprises multiple pillars, each one of which is separated from an adjacent pillar or an inner surface of said compartment (103) by a space that is smaller than the microbeads' diameter.

17. The cell-free system (100) of claim 1, wherein the inner surface of said barrier comprises a first functional group of a specific binding pair capable of binding to a complementary second functional group of said binding pair present on said DNA or modified DNA, and is therefore designed to bind to said DNA or modified-DNA.

18. The cell-free system (100) of claim 1, wherein said translation compartment (102) comprises microbeads capable of binding said protein and a physical obstacle designed to prevent passage of said microbeads therethrough.

19. The cell-free system (100) of claim 18, wherein said physical obstacle
comprises multiple pillars, each one of which is separated from an adjacent pillar or an inner surface of said compartment (102) by a space that is smaller than the microbeads' diameter.

20. The cell-free system (100) of claim 18, wherein said microbeads comprise a transition metal ion having high affinity to His-tag.

21. The cell-free system (100) of claim 1, wherein said compartment (102) further comprises ribosomes and/or translation components.

22. The cell-free system (100) of claim 1, wherein the inner surface of said translation compartment (102) comprises a first functional group of a specific binding pair capable of binding to a complementary second functional group of said binding pair present on said protein, and is therefore designed to bind to said protein.

23. The cell-free system (100) of claim 1, wherein said compartment (102) comprises a physical obstacle designed to prevent passage of said microbeads therethrough.

24. The cell-free system (100) of claim 1, further comprising at least one
valve that controls flow or flow rate.

25. The cell-free system (100) of claim 1, comprising one or more additional DNA transcription compartments (101) each comprising a fluid inlet port (101*a*) and a fluid outlet port (101*b*), and fluidly connected to said translation compartment (102).

26. The cell-free system (100) of claim 1, comprising one or more additional translation compartments (102), each fluidly connected to a different DNA transcription compartment (101).

27. A method of producing a protein, said method comprising:
(i) providing a cell-free system (100) as defined in claim 1;
(ii). injecting DNA or modified-DNA into the fluid inlet port (101*a*) of said compartment (101);
(iii) incubating the system (100) for a sufficient time and temperature for transcription of said DNA to mRNA;
(iv) injecting washing buffer into said fluid inlet port (101*a*) to separate newly produced mRNA from said DNA or modified-DNA and transferring said mRNA to the translation and post-translational modification (PTM) compartment (102);
(v) incubating the system (100) for a sufficient time and temperature for enabling translation of said m RNA to protein; and
(vi) injecting elution buffer to elute the protein, to thereby producing said protein,
wherein, provided that when said system (100) does not comprise:
a RNA polymerase, the method further includes a step of injecting RNA polymerase or microbeads with an RNA polymerase bound thereon into said fluid inlet port (101*a*), after step (i) and prior to step (ii);
a DNA-binding molecule, the method further includes a step of injecting microbeads with a binding molecule capable of selectively binding DNA or modified-DNA into a fluid inlet port of said compartment (101) or a separate barrier compartment prior to step (iv);
a protein-binding molecule, the method further includes a step of injecting microbeads capable of binding the protein obtained in step (v), into said translation compartment (102) prior to step (v); and
ribosomes and reagents necessary for mRNA translation, the method further includes a step of injecting ribosomes and reagents necessary for mRNA translation into said translation compartment (102), prior to step (v).

28. The method of claim 27 for producing a protein, said method comprising:
(i) providing a cell-free system (100) as defined in claim 1, which does not include RNA polymerase, DNA-binding molecule and protein-binding molecule;
(ii) injecting RNA polymerase or microbeads binding an RNA polymerase into said fluid inlet port (101*a*) of said compartment (101);
(iii) injecting microbeads binding a molecule capable of selectively binding DNA or modified-DNA into a fluid inlet port of said compartment (101) or a separate barrier compartment;
(iv) injecting microbeads capable of binding said protein, and ribosomes and reagents necessary for mRNA translation into said compartment (102);
(v) injecting DNA or modified-DNA into said fluid inlet port of said compartment (101);
(vi) incubating the system (100) for a sufficient time and temperature for transcription of said DNA to mRNA;
(vii) injecting wash buffer into said fluid inlet port of said compartment (101) to separate newly produced mRNA from said DNA or modified-DNA and transferring said mRNA to said translation and PTM compartment (102);
(viii) incubating the system (100) for a sufficient time and temperature for enabling translation of said m RNA into protein; and
(ix) injecting elution buffer to elute the protein, thereby producing said protein.

29. The method of claim 27, for producing a post-translational modified (PTM) protein, said method further comprising the following steps after step (v) and prior to step (vi):
injecting wash buffer into said fluid inlet port (102*a*) of said compartment (102) to remove cell-free translation components and mRNA;
(ii) injecting post-translation modification enzyme(s) and substrate into said translation and PTM compartment (102), if said system (100) does not comprise same;
(iii) incubating the system (100) for a sufficient time and temperature for enabling PTM of the protein; and
(iv) injecting wash buffer into said fluid inlet port of said compartment (102) to remove post-translation modification enzyme(s) and substrate(s);
thereby producing said post-translation modified protein.

30. A kit comprising:
(i) said cell-free system (100) of claim 1; and
(ii) a leaflet with instructions for expressing a DNA molecule and optionally performing PTM using said cell-free system (100).

31. The kit of claim 30, further comprising at least one of:
(iii) a vessel comprising RNA polymerase or RNA polymerase immobilized on microbeads;
(iv) a vessel comprising DNA-binding molecule or modified-DNA-binding molecule immobilized on microbeads;
(v) a vessel comprising cell-free translation components;
(vi) a vessel comprising microbeads designed to immobilize protein; and
(vii) vessels comprising solutions comprising factors necessary for producing RNA and protein, and optionally PTM of said protein.

32. The kit of claim 30, further comprising:
(iii) a vessel comprising washing solution; and/or
(iv) a vessel comprising elution solution.

33. The kit of claim 30 comprising:
(i) said cell-free system (100) of claim 1;
(ii) a vessel comprising RNA polymerase immobilized on microbeads;
(iii) a vessel comprising DNA-binding molecule or modified-DNA-binding molecule immobilized on microbeads;
(iv) a vessel comprising cell-free translation components;
(v) a vessel comprising microbeads designed to immobilize protein;
(vi) vessels comprising solutions comprising factors necessary for producing RNA and protein, and optionally PTM of said protein;
(vii) a leaflet with instructions for expressing a DNA molecule and optionally performing PTM using said cell-free system (100);
(viii) optionally, a vessel comprising washing solution; and
(ix) optionally a vessel comprising elution solution.

* * * * *

SEQUENCE LISTING

```
<160> NUMBER OF SEQ ID NOS: 11

<210> SEQ ID NO 1
<211> LENGTH: 18
<212> TYPE: DNA
<213> ORGANISM: Artificial Sequence
<220> FEATURE:
<223> OTHER INFORMATION: synthetic

<400> SEQUENCE: 1
taatacgact cactatag                                                   18

<210> SEQ ID NO 2
<211> LENGTH: 48
<212> TYPE: DNA
<213> ORGANISM: Artificial Sequence
<220> FEATURE:
<223> OTHER INFORMATION: synthetic
```

```
<400> SEQUENCE: 2
ctagcataac cccttggggc tctaaacgg gtcttgaggg gttttttg            48

<210> SEQ ID NO 3
<211> LENGTH: 128
<212> TYPE: DNA
<213> ORGANISM: Artificial Sequence
<220> FEATURE:
<223> OTHER INFORMATION: synthetic

<400> SEQUENCE: 3
ggatgcgtaa ccctcaagga acccgcaagc catcgggact caagccgccg gtacctccga   60
agggacggtg cggagaggag aggggcact gggcggctgt gtgagattct gccaaataga   120
cagccgaa                                                           128

<210> SEQ ID NO 4
<211> LENGTH: 38
<212> TYPE: DNA
<213> ORGANISM: Artificial Sequence
<220> FEATURE:
<223> OTHER INFORMATION: synthetic

<400> SEQUENCE: 4
ggatcccgac tggcgagagc caggtaacga atggatcc                          38

<210> SEQ ID NO 5
<211> LENGTH: 774
<212> TYPE: DNA
<213> ORGANISM: Artificial Sequence
<220> FEATURE:
<223> OTHER INFORMATION: synthetic

<400> SEQUENCE: 5
atgggcagca gccatcatca tcatcatcac agcagcggcc tgtgccgcg cggcagccat   60 atggtgagca agggcgagga gctgttcacc ggggtggtgc ccatcctggt cgagctggac   120
ggcgacgtaa acggccacaa gttcagcgtg tccggcgagg gcgagggcga tgccacctac   180
ggcaagctga ccctgaagtt catctgcacc accggcaagc tgcccgtgcc ctggcccacc   240
ctcgtgacca ccctgaccta cggcgtgcag tgcttcagcc gctaccccga ccacatgaag   300
cagcacgact tcttcaagtc cgccatgccc gaaggctacg tccaggagcg caccatcttc   360
ttcaaggacg acggcaacta caagacccgc gccgaggtga agttcgaggg cgacaccctg   420
gtgaaccgca tcgagctgaa gggcatcgac ttcaaggagg acggcaacat cctgggcac   480 aagctggagt acaactacaa cagccacaac gtctatatca tggccgacaa gcagaagaac   540
ggcatcaagg tgaacttcaa gatccgccac aacatcgagg acggcagcgt gcagctcgcc   600
gaccactacc agcagaacac ccccatcggc gacggccccg tgctgctgcc cgacaaccac   660
tacctgagca cccagtccgc cctgagcaaa gaccccaacg agaagcgcga tcacatggtc   720
ctgctggagt tcgtgaccgc cgccgggatc actctcggca tggacgagct gtag         774

<210> SEQ ID NO 6
<211> LENGTH: 483
<212> TYPE: DNA
<213> ORGANISM: Artificial Sequence
<220> FEATURE:
<223> OTHER INFORMATION: synthetic

<400> SEQUENCE: 6
atgggcagca gccatcatca tcatcatcac agcagcggcc tgtgccgcg cggcagccat   60
```

```
atggatgtat tcatgaaagg actttcaaag gccaaggagg gagttgtggc tgctgctgag    120
aaaaccaaac agggtgtggc agaagcagca ggaaagacaa aagagggtgt tctctatgta    180
ggctccaaaa ccaaggaggg agtggtgcat ggtgtggcaa cagtggctga aagaccaaa     240 gagcaagtga caaatgttgg aggagcagtg gtgacgggtg tgacagcagt agcccagaag    300
acagtggagg gagcagggag cattgcagca gccactggct ttgtcaaaaa ggaccagttg    360
ggcaagaatg aagaaggagc cccacaggaa ggaattctgg aagatatgcc tgtggatcct    420
gacaatgagg cttatgaaat gccttctgag gaagggtatc aagactacga acctgaagcc    480
tag                                                                   483
```

<210> SEQ ID NO 7
<211> LENGTH: 20
<212> TYPE: PRT
<213> ORGANISM: Artificial Sequence
<220> FEATURE:
<223> OTHER INFORMATION: biotin-binding peptide
<220> FEATURE:
<221> NAME/KEY: misc_feature
<223> OTHER INFORMATION: synthetic

<400> SEQUENCE: 7

Ala Glu Gly Glu Phe Cys Ser Trp Ala Pro Pro Lys Ala Ser Cys Gly
1               5                   10                  15

Asp Pro Ala Lys
            20

<210> SEQ ID NO 8
<211> LENGTH: 11
<212> TYPE: PRT
<213> ORGANISM: Artificial Sequence
<220> FEATURE:
<223> OTHER INFORMATION: biotin-binding peptide
<220> FEATURE:
<221> NAME/KEY: misc_feature
<223> OTHER INFORMATION: synthetic

<400> SEQUENCE: 8

Cys Ser Trp Arg Pro Pro Phe Arg Ala Val Cys
1               5                   10

<210> SEQ ID NO 9
<211> LENGTH: 11
<212> TYPE: PRT
<213> ORGANISM: Artificial Sequence
<220> FEATURE:
<223> OTHER INFORMATION: biotin-binding peptide
<220> FEATURE:
<221> NAME/KEY: misc_feature
<223> OTHER INFORMATION: synthetic

<400> SEQUENCE: 9

Cys Ser Trp Ala Pro Pro Phe Lys Ala Ser Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: biotin-binding peptide
<220> FEATURE:
<221> NAME/KEY: misc_feature
<223> OTHER INFORMATION: synthetic

```
<400> SEQUENCE: 10

Cys Asn Trp Thr Pro Pro Phe Lys Thr Arg Cys
1               5                   10

<210> SEQ ID NO 11
<211> LENGTH: 140
<212> TYPE: PRT
<213> ORGANISM: Artificial Sequence
<220> FEATURE:
<223> OTHER INFORMATION: alpha-synuclein
<220> FEATURE:
<221> NAME/KEY: misc_feature
<223> OTHER INFORMATION: synthetic

<400> SEQUENCE: 11

Met Asp Val Phe Met Lys Gly Leu Ser Lys Ala Lys Glu Gly Val Val
1               5                   10                  15

Ala Ala Ala Glu Lys Thr Lys Gln Gly Val Ala Glu Ala Ala Gly Lys
                20                  25                  30

Thr Lys Glu Gly Val Leu Tyr Val Gly Ser Lys Thr Lys Glu Gly Val
            35                  40                  45

Val His Gly Val Ala Thr Val Ala Glu Lys Thr Lys Glu Gln Val Thr
    50                  55                  60

Asn Val Gly Gly Ala Val Val Thr Gly Val Thr Ala Val Ala Gln Lys
65                  70                  75                  80

Thr Val Glu Gly Ala Gly Ser Ile Ala Ala Ala Thr Gly Phe Val Lys
                85                  90                  95

Lys Asp Gln Leu Gly Lys Asn Glu Glu Gly Ala Pro Gln Glu Gly Ile
            100                 105                 110

Leu Glu Asp Met Pro Val Asp Pro Asp Asn Glu Ala Tyr Glu Met Pro
        115                 120                 125

Ser Glu Glu Gly Tyr Gln Asp Tyr Glu Pro Glu Ala
        130                 135                 140
```